US012746039B2

(12) United States Patent
Diebo et al.

(10) Patent No.: US 12,746,039 B2
(45) Date of Patent: Sep. 29, 2026

(54) AUTOMATED MACHINE LEARNING DESIGN OF ORTHOPEDIC IMPLANTS AND METHODS FOR USING SAME

(71) Applicant: Spinal Alignment Solutions, Inc., Wilmington, DE (US)

(72) Inventors: Bassel G. Diebo, East Providence, RI (US); Alan H. Daniels, East Providence, RI (US); Miles C. Wilson, Tiverton, RI (US)

(73) Assignee: SPINAL ALIGNMENT SOLUTIONS, INC., Wilmington, NC (US)

( * ) Notice: Subject to any disclaimer, the term of this patent is extended or adjusted under 35 U.S.C. 154(b) by 0 days.

(21) Appl. No.: 19/026,236

(22) Filed: Jan. 16, 2025

(65) Prior Publication Data

US 2025/0160899 A1 May 22, 2025

Related U.S. Application Data

(63) Continuation of application No. PCT/US2024/014680, filed on Feb. 6, 2024.

(Continued)

(51) Int. Cl.

*A61B 17/70* (2006.01)
*A61B 5/00* (2006.01)

(Continued)

(52) U.S. Cl.

CPC ........ *A61B 17/7011* (2013.01); *A61B 5/1071* (2013.01); *A61B 5/407* (2013.01);

(Continued)

(58) Field of Classification Search

CPC ............ A61B 17/7004; A61B 17/7011; A61B 17/7013

See application file for complete search history.

(56) References Cited

U.S. PATENT DOCUMENTS 11,553,969 B1 1/2023 Lang et al.
2008/0077136 A1* 3/2008 Triplett .............. A61B 17/7004 606/86 A (Continued)

FOREIGN PATENT DOCUMENTS

WO 2023186625 A1 10/2023

OTHER PUBLICATIONS

International Search Report and Written Opinion for PCT International Patent Application No. PCT/US2024/014680, mailed Aug. 12, 2024.

*Primary Examiner* — Julianna N Harvey
(74) *Attorney, Agent, or Firm* — Adler Pollock & Sheehan P.C.

(57) ABSTRACT

Machine learning techniques are disclosed for making of spinal fixation rods and other custom orthopedic implants with preferred, long-term surgical outcomes, each implant with a shape predicted by multiple layers of trained convoluted neural networks, mainly for use in a spinal surgery on a subject's spine. The rods provide predictable long-term outcomes for the patients. The rods include a curvature that is matched to the features of matching a unique curvature of the subject's spine; matching a preferred outcome from a large data set of improved patients; and matching a machine learning algorithm for two or more tulip head screw position markings on the rod operative to ensure an execution of a surgical plan following the rod's established contour. The implants can be configured in a kit ready for use by a surgeon in a surgical procedure.

5 Claims, 30 Drawing Sheets

Related U.S. Application Data

(60) Provisional application No. 63/614,244, filed on Dec. 22, 2023, provisional application No. 63/497,949, filed on Apr. 24, 2023, provisional application No. 63/483,728, filed on Feb. 7, 2023.

(51) Int. Cl.
*A61B 5/107* (2006.01)
*A61B 34/10* (2016.01)

(52) U.S. Cl.
CPC ...... *A61B 17/7002* (2013.01); *A61B 17/7013* (2013.01); *A61B 34/10* (2016.02); *A61B 17/7004* (2013.01); *A61B 2034/107* (2016.02)

(56) References Cited

U.S. PATENT DOCUMENTS

| | | | | |
|---|---|---|---|---|
| 2016/0235479 | A1* | 8/2016 | Mosnier | A61B 17/8863 |
| 2016/0310289 | A1* | 10/2016 | Arlet | A61F 2/4455 |
| 2017/0119281 | A1 | 5/2017 | Hermann | |
| 2017/0135706 | A1* | 5/2017 | Frey | A61B 17/1671 |
| 2018/0317970 | A1* | 11/2018 | Lomeli | C25D 11/022 |
| 2019/0362028 | A1* | 11/2019 | Mosnier | A61B 17/7011 |
| 2022/0013211 | A1 | 1/2022 | Steinberg et al. | |

* cited by examiner

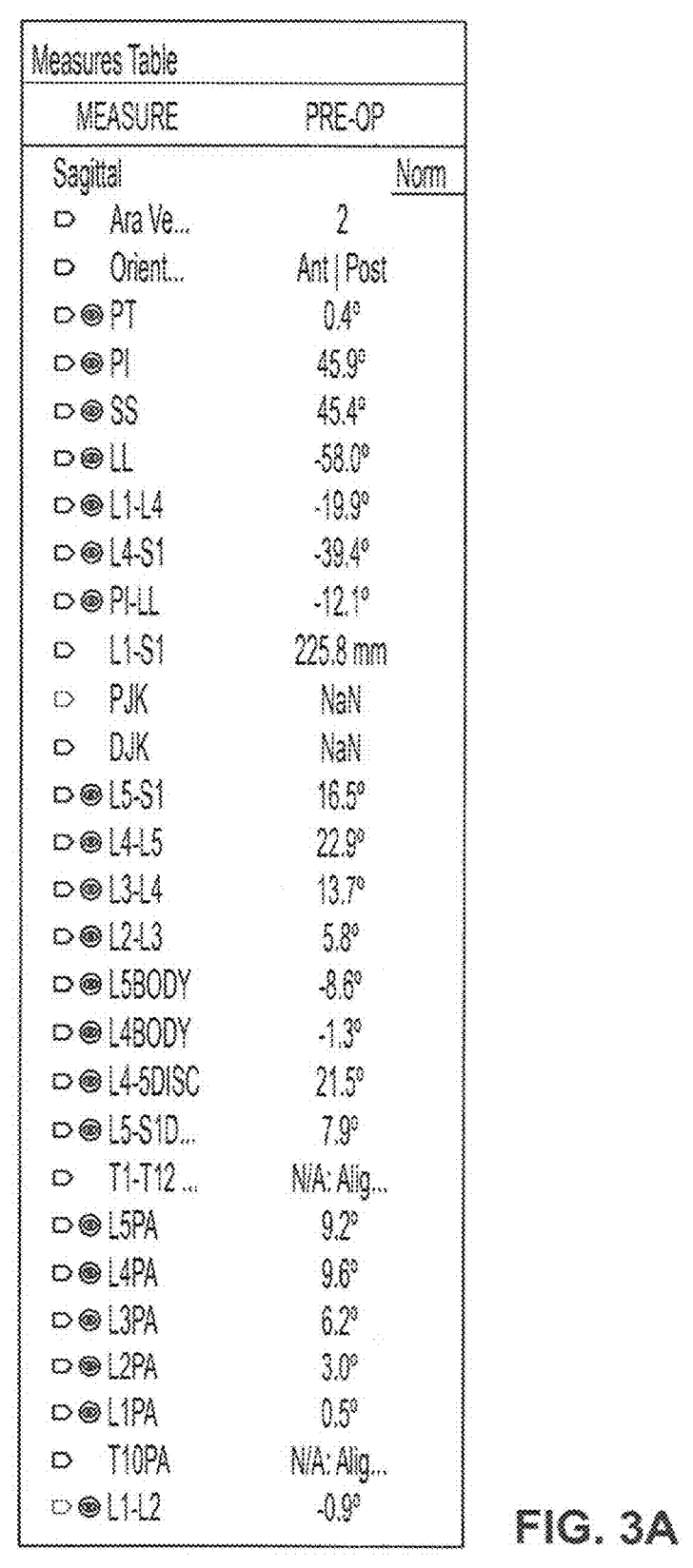

Measures Table

| MEASURE | PRE-OP | |
|---|---|---|
| Sagittal | | Norm |
| Ara Ve... | 2 | |
| Orient... | Ant \| Post | |
| PT | 0.4° | |
| PI | 45.9° | |
| SS | 45.4° | |
| LL | -58.0° | |
| L1-L4 | -19.9° | |
| L4-S1 | -39.4° | |
| PI-LL | -12.1° | |
| L1-S1 | 225.8 mm | |
| PJK | NaN | |
| DJK | NaN | |
| L5-S1 | 16.5° | |
| L4-L5 | 22.9° | |
| L3-L4 | 13.7° | |
| L2-L3 | 5.8° | |
| L5BODY | -8.6° | |
| L4BODY | -1.3° | |
| L4-5DISC | 21.5° | |
| L5-S1D... | 7.9° | |
| T1-T12 ... | N/A: Alig... | |
| L5PA | 9.2° | |
| L4PA | 9.6° | |
| L3PA | 6.2° | |
| L2PA | 3.0° | |
| L1PA | 0.5° | |
| T10PA | N/A: Alig... | |
| L1-L2 | -0.9° | |

FIG. 3A

Under Revision

AUTOMATED MACHINE LEARNING DESIGN OF ORTHOPEDIC IMPLANTS AND METHODS FOR USING SAME

CROSS-REFERENCE TO RELATED APPLICATIONS

This application claims the benefit of priority to United States (US) provisional application Ser. No. 63/483,728, filed Feb. 7, 2023, the disclosure of which is incorporated by reference as if fully set forth herein in its entirety. This application also claims the benefit of priority to U.S. provisional application Ser. No. 63/497,949, filed Apr. 24, 2023, the disclosure of which is incorporated by reference as if fully set forth herein in its entirety. In addition, this application claims the benefit of priority to U.S. provisional application Ser. No. 63/614,244, filed Dec. 22, 2023, the disclosure of which is incorporated by reference as if fully set forth herein in its entirety.

FIELD OF THE INVENTION

The embodiments of the present invention relate to machine learning and software design of smart orthopedics, and more particularly, to machine learning designed spinal rods and cages and methods for using these implants in planned surgeries.

BACKGROUND OF THE INVENTION

Spinal defects may be caused by various conditions such as genetics, fractures, environmental factors, Marfan syndrome, neurofibromatosis, neuromuscular diseases, severe injuries, scoliosis, diseases of aging (e.g., soft tissue, muscle quality and bone loss), infections, slipped discs, and tumors. It is generally known that the intervertebral discs are soft tissues that sit between each vertebra and act as cushions between vertebrae, and absorb energy while the spinal column flexes, extends, and twists. Nerves from the spinal cord exit the spinal column from the spine and extending out between each vertebra. As such, any defects in the spine can quickly result in a nerve compression, severe pain, immobilization, and paralysis.

Correction of spinal conditions may involve spine surgery. Spinal fusion is one surgical technique in which one or more vertebrae are fused together to stop the motion between them, which is often a pain generator via degenerative cascade, pinched nerves or deterioration of spinal shape in one or more dimensions. Spinal fusion often involves insertion of pedicles screws and longitudinal rods that connect on the screw heads to stabilize the spine and form the new spine shape. Surgical treatment aims for decompression of the neural elements and realignment of the spine if needed. The new spinal shape is permanent, and the goal is for it to last for a lifetime. While pedicle screws and rods are connected to the vertebrae, spine surgery can also use one or more interbody devices that are placed in between the vertebrae in lieu of the removed or treated disc level. Interbody fusion uses a hollow threaded titanium or carbon fiber cylinder to fuse two vertebrae together. The diseased disc is removed, and two interbody cages are placed in the opening where the diseased disc has been removed. The cages can be filled with bone graft. The surrounding bones grows through the holes in the cages, fusing the vertebrae.

In general, interbody cages are typically cylindrical or box-shaped, hollow, and porous metallic devices that are placed between two adjacent vertebrae in a spinal segment after removing a damaged disc. The cage may occupy the entire disc space or just a front (anterior) part of it. To reiterate, connecting rods and pedicle screws are used in a spinal fusion to add extra support and strength to the fusion while it heals. The rod is used to connect the screws which prevents movement and allows the bone graft to heal. While the spinal rods provide support to the fused spine for a patient's motion, the rods still do not correct the spine to a preferred state. Common issues in spinal surgery are high reoperation and biomechanical complications. Complications arise from poorly shaped fused spine with unsustainably inappropriate shape. What is urgently needed are intelligently designed spinal rods, and interbody cages and methods of implementing them in pre-planned spinal surgeries; this will ensure systematic treatment and proper spinal shape when patients undergo fusion surgery.

BRIEF SUMMARY OF THE INVENTION

The following presents a simplified summary of the innovation in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

In a broad embodiment, a huge problem in spinal surgeries is that the conventional rods (human-bent or currently manufactured worldwide) spinal rods do not meticulously follow the proper curvature of the human spine. In one example, a conventional spinal rod cannot follow the natural lordosis of the lower back (i.e., the back-waist curve). After surgery, studies revealed that about 50% of spinal surgery performed produce rods that are straightened out or overbent into an unnatural position. At first, the unfused spinal segments compensate for the improper rod contour effects, but eventually the discs above and/or below the fusion degenerate and wear down. The patient then develops back pain, has difficulty standing upright, and experiences limitations when walking. Eventually, the problem requires yet another major surgery to realign the spine. Thus, the presently disclosed technology provides machine learning in various layers of convolutional neural networks to provide pre-planned shapes, contours, curvatures, and sizes to spinal rods (and associated hardware) that enable a surgeon to plan a desired surgical outcome for the patient. This brings great relief to patients, especially over a long-term of 2 or more years, and continues for a lifetime.

In one aspect, the invention features a spinal fixation rod for use in surgery on a patient's spine that includes a curvature configured to match the patient's unique spine shapes. These shapes can be determined by the morphology of the pelvis for each patient, often assessed using pelvic incidence radiographic parameter. There can be markings in certain spaced locations along a length of the rod, the markings configured to enable precise alignment of the rod with the tulip head of a pedicle screw during surgery. Standardizing the intersection between the tulip head and the rod will enable accurate execution of the surgical plan and the shape dictated by the invented rods.

In one embodiment, a method comprising the following is disclosed: in a computer system having at least a processor and a memory, receiving data representing a surgical assessment of a subject; receiving data indicative of the subject's spine; receiving data indicative of the subject's tissues associated with the spine; receiving data indicative of the subject's tissues surrounding the spine; superimposing a shape of a rod with the data indicative of the subject's assessment, the subject's spine, the subject's tissues associated with the spine, and the subject's tissues surrounding the spine; and in response to the superimposition, adjusting the shape of the rod to achieve a surgical outcome of implanting the rod into the subject's spine.

According to some aspects, the method disclosed above can be wherein the rod includes markings. In this example, a configuration of the markings can be planned to match the subject's spinal curvature, pelvic incidence, and vertebrae positions. The configuration can be computed from at least the data indicative of the subject's assessment, the subject's spine, the subject's tissues associated with the spine, and the subject's tissues surrounding the spine. In this example, the configuration is can be, in some embodiments, further computed using one or more artificial intelligence (AI) methods. In some embodiments, the data representing the surgical assessment of the subject includes a sagittal profile of the subject as a result of using lumbar or full body standing radiographs. According to some aspects, the data representing the surgical assessment of the subject includes a pelvic incidence measurement.

In some embodiments, the method disclosed above can be further comprising implanting an interbody device in the subject's spine, the interbody device having a size, a lordosis and a height configured to fit a new alignment, contour, and shape of the spine. According to some aspects, the method is executed wherein the one or more artificial intelligence (AI) methods are utilized to determine tulip head positions on the spinal alignment rod.

According to some aspects, the method disclosed above is executed wherein a tulip head offset from one or more vertebral bodies is planned based on the data indicative of the subject's assessment, the subject's spine, the subject's tissues associated with the spine, and the subject's tissues surrounding the spine. In this example, the method can be executed further comprising generating a screw trajectory and a tulip/rod intersection using navigation, robotic assistance, and ultrasound input.

In some embodiments, the one or more markings on the rod are used to lock the rod into a tulip head of pedicle screws. In this example, one or more additional markings on the rod indicate a cutting point for a surgeon to cut the rod at an optimum location.

According to some aspects, the invention features an orthopedic implant including a singular, asymmetric frame having anterior and posterior portions, superior and inferior surfaces, and two opposing sides, the superior and inferior surfaces asymmetric with respect to a center line passing through the opposing sides. The rod discussed above can dictate the shape and/or angles in the implant.

In some embodiments, a method of treating a subject in need of a spinal surgery is provided herein, the method comprising the steps of: (1) performing and/or obtaining a surgical assessment of the subject; (2) obtaining data from the subject's spine, tissues associated with the spine, and/or surrounding tissues; and (3) superimposing a shape of a rod with the data and/or with another dataset derived from clinical data, and adjusting the shape to a preferred surgical outcome shape; whereby a rod suitable to achieve the preferred surgical outcome is obtained and is operable to be implanted into the subject's spine.

According to some aspects, the method is further comprising placing or positioning one or more markings on the rod wherein a configuration of the markings is operative to match the unique subject's spinal curvature, pelvic incidence, and/or vertebrae position(s) because the rod is made using data from the patient's spine and surrounding tissue and an algorithm. The algorithm can be a software algorithm, machine learning algorithm, and/or an artificial intelligence algorithm.

The method can be further comprising one or more of the following steps of surgical planning methods are executed (at any order or at any place in the method):

A sagittal profile of the subject is assessed using lumbar, 36 inch (91.4 cm), and/or full body standing radiographs; a pelvic incidence (PI) of the subject is measured by a human or semi-automatically or fully automatically using a dedicated software with a machine learning algorithm; one or more radiographs are loaded on a surgical planning software; a rod contour is planned; an interbody device size, lordosis, and/or height is planned to fit the new alignment/contour/shape of the spine; a data-driven, artificial-intelligence, and/or machine-learning process is utilized to determine tulip head positions on the rod to ensure perfect execution of the surgical plan following the established rod contour; a tulip head offset from one or more vertebral bodies is also planned based on a data driven, proprietary data set generated from patients with significant improvement of their alignment, patient reported outcomes and have no revision surgery or mechanical complications at 2 years follow up; and a screw trajectory and/or a tulip/rod intersection is planned using free-hand, navigation, robotic assistance, and/or ultrasound guidance.

The method discussed above can be further comprising an intraoperative verification of the surgical plan is performed including one or more of measuring segmental lordosis and offset from assigned targets using cellphone, radiography, fluoroscopy, computerized tomography (CT), robotics, and/or ultrasound.

According to some aspects, the method is further comprising a pre-operative surgical plan is assessed using one or more of a healthcare provider's examination of the subject, an ultrasound, navigation system, and/or a robotic assisted exam.

In some embodiments, the method is further comprising a post-operative surgical assessment is executed using one or more of a healthcare provider's examination of the subject, an ultrasound, navigation system, and/or a robotic assisted exam.

According to some aspects, the method is executed wherein one or more rods are matched to the patient's pelvic incidence (PI) number.

In some embodiments, the method is executed wherein a surgeon makes one or more anatomical measurements to determine the proper spinal shape in harmony with the patient morphology of the pelvis and spine According to some aspects, the method above is executed wherein one or more rods are configured to fit into the desired angulation and allow the surgeon to lock down the spine in patient-specific place using pedicle screws.

In some embodiments, the method is executed wherein one or more markings on a rod are used to lock the rod into a tulip head of the pedicle screws.

According to some aspects, the method can be executed wherein a rod for an implantation in the subject is selected be a human being, by a surgical planning software, or a combination thereof.

In some embodiments, the method can be executed wherein there are one or more additional markings on rod to indicate a cutting point for the surgeon to cut the rod at an optimum location.

These and other features and advantages will be apparent from a reading of the following detailed description and a review of the associated drawings. It is to be understood that both the foregoing general description and the following detailed description are explanatory only and are not restrictive of aspects as claimed.

Other implementations are also described and recited herein. These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

Solely for the purpose of illustration, certain embodiments of the present invention are explained using examples in the drawings described below. It should be understood, however, that the invention is not limited to the precise arrangements, dimensions, and configurations shown. In the drawings:

Introductory basics to a spinal fusion to correct defects (using currently available technology) are shown.

FIG. 3A shows an example of measurements performed (by a healthcare provider or a surgeon) on a subject in need of a spinal surgery and recorded in a Measures Table. At the left column are indicated specific vertebral regions and determinative angles, and at the right column are the values measured.

From the technology disclosed herein.

Figure 1:
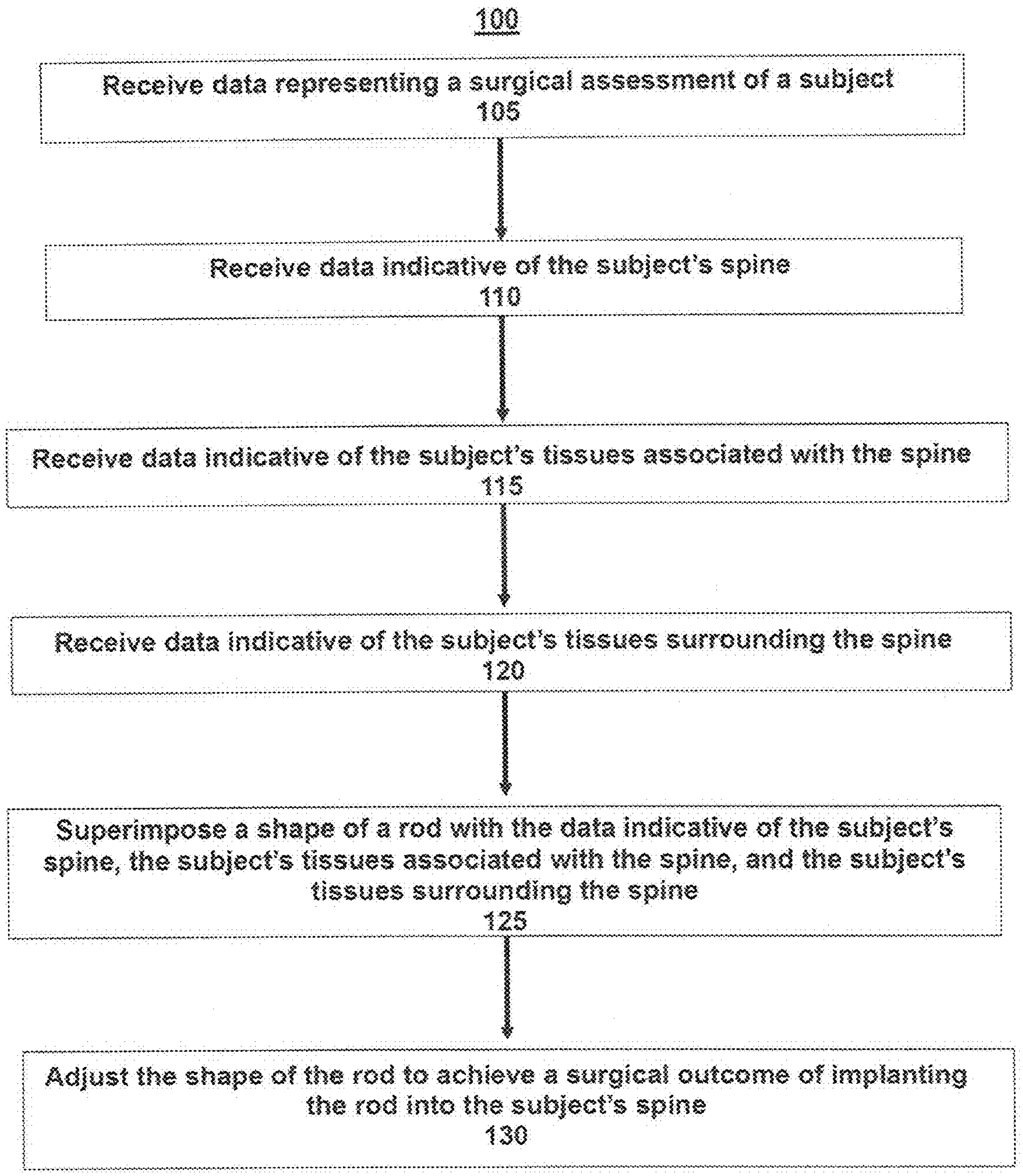
FIG. 1 shows an example process 100 of treating a subject in need of a spinal surgery includes receiving data 105 representing a surgical assessment of a subject, receiving data 110 indicative of the subject's spine, receiving data 115 indicative of the subject's tissues associated with the spine, and receiving data 120 indicative of the subject's tissues surrounding the spine. Process 100 superimposes 125 a shape of a rod with the data indicative of the subject's spine, the subject's tissues associated with the spine, and the subject's tissues surrounding the spine. Process 100 adjusts 130 the shape of the rod to achieve a surgical outcome of implanting the rod into the subject's spine. Any of the steps can be omitted as need or combined with other methods disclosed herein.

All trademarks, images, likenesses, words, and depictions in the drawings and the disclosure are plainly in fair use and are provided solely for the purposes of illustration of the invention in view of an urgent need to treat subjects as further discussed in detail below.

DETAILED DESCRIPTION OF THE INVENTION

The subject innovation is now described in some instances, when necessary, with reference to the drawings. In the following description, for purposes of explanation, numerous specific details are set forth in order to provide a thorough understanding of the present invention. It may be evident, however, that the present invention may be practiced without these specific details. In other instances, well-known structures, methods, and devices are shown in block diagram form or with illustrations in order to facilitate describing the present invention. It is to be appreciated that certain aspects, modes, embodiments, variations and features of the invention are described below in various levels of detail in order to provide a substantial understanding of the present invention.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail. In general, typical chemical terminology is found in the International Union of Pure and Applied Chemistry GoldBook[2]. This disclosure is purposefully presented in commonly understood words, known to a person of skill in the art, but Merriam-Webster's Online Dictionary is used, when appropriate, for terms not specifically demonstrated herein or not known in the art[3].

As used in this specification and the appended claims, the singular forms "a," "an" and "the" include plural referents unless the content clearly dictates otherwise. For example, reference to "a cell" includes a combination of two or more cells, and the like.

As used herein, the term "approximately" or "about" in reference to a value or parameter are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value). As used herein, reference to "approximately" or "about" a value or parameter includes (and describes) embodiments that are directed to that value or parameter. For example, description referring to "about X" includes description of "X".

As used herein, the term "or" means "and/or." The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the term "comprising" means that other elements can also be present in addition to the defined elements presented. The use of "comprising" indicates inclusion rather than limitation. The term "including" can be interchanged with "comprising".

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention. The term "consisting essentially of" can also be exemplified by plain language provided in the claims.

As used herein, the term "spinal fusion cage" can be used interchangeably with "interbody cages".

The term "statistically significant" or "significantly" refers to statistical significance and generally means a two-standard deviation (2SD) or greater difference.

As used herein, the term "subject" refers to a mammal, including but not limited to a dog, cat, horse, cow, pig, sheep, goat, rodent, or primate. Subjects can be house pets (e.g., dogs, cats), agricultural stock animals (e.g., cows, horses, pigs, chickens, etc.), laboratory animals (e.g., mice, rats, rabbits, etc.), but are not so limited. Subjects particularly include human subjects in urgent treatment as described herein. The human subject may be a pediatric, adult, or a geriatric subject. The human subject may be of any sex.

The term "treating" includes prophylactic and/or therapeutic treatments. The term "prophylactic or therapeutic" treatment is art-recognized and includes administration to the host of one or more of the subject compositions and/or application of one or more therapies or surgeries. If this is done prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

As used herein, the terms "treat," "treatment," "treating," or "amelioration" when used in reference to a disease, disorder, or medical condition, refer to therapeutic treatments for a condition, wherein the object is to reverse, alleviate, ameliorate, inhibit, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a condition is reduced or halted. That is, "treatment" includes not just the improvement of symptoms or markers, but also a cessation or at least slowing of progress or worsening of symptoms that would be expected in the absence of treatment. Beneficial or desired clinical results include, but are not limited to, alleviation of one or more symptom(s), sign(s), diminishment of extent of the deficit, stabilized (i.e., not worsening) state of a symptom or condition, delay or slowing of onset of symptoms or indications, and an increased lifespan as compared to that expected in the absence of treatment.

The terms: "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g., the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

In some embodiments, the decrease in the one or more signs or symptoms is evaluated according to a specialized healthcare provider. In some embodiments, signs are observed or measured by a health care provider. Symptoms can be reported by the subject. In some embodiments, the decrease of signs or symptoms occurs in less than about 120 minutes, 90 minutes, less than about 60 minutes, less than about 30 minutes, less than about 15 minutes, less than about 10 minutes, or less than about 5 minutes, or less than about 3 minutes, or less than about 1 minute. In some embodiments, the decrease of signs or symptoms occurs in less than 1 day, less than 1 week, less than 1 month, or in less than 1 year.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, an agent or a therapeutic agent provided to a subject and suspected to be or involved in a treatment can be a small molecule less than 1000 MW or a large molecule not less than 1000 MW including biologics, oligonucleotides, peptides, oligosaccharides, and larger molecules. Any of the therapeutic agents disclosed herein can be used as or in combination with small molecules and/or large molecules as discussed herein.

A subject can be one who has been previously diagnosed with or identified as suffering from or having a condition in need of treatment (e.g., a scoliosis, spinal deformity, spinal stenosis, spondylolisthesis, or related disorder) or one or more complications related to such a condition, and optionally, but need not have already undergone treatment for a condition or the one or more complications related to the condition. Alternatively, a subject can also be one who has not been previously diagnosed as having a condition in need of treatment or one or more complications related to such a condition. For example, a subject can be one who exhibits one or more risk factors for a condition, or one or more complications related to a condition or a subject who does not exhibit risk factors. A "subject in need" of treatment for a particular condition can be a subject having that condition, diagnosed as having that condition, suspected as having, or at risk of developing that condition. In another example, the subject has been brought into a treatment situation entirely without the subject's knowledge and/or intent. For example, a subject can obviously be in need of treatment but not be responsive to an immune checkpoint inhibitor, and as described herein the present methods and formulations may save the subject's life.

A spinal fixation rod can be a material spanning two or more vertebrae. Pedicle screws help secure rods and/or plates to the spinal segment(s) during a spinal fusion surgery. Pedicle screws are threaded FDA (US Food and Drug Agency) or a national health authority approved material (e.g., titanium, cobalt, chrome, or stainless-steel) implants that are fastened through the vertebral pedicles located at the back of the spinal bones. The screws act as anchor points and are typically positioned at 2 or more consecutive spinal segments connected by a rod. Rod shape can dictate the spinal shape and can be derived specifically for the patient using the patient's pelvic incidence. The tulip head of a pedicle screw is a point of attachment for a rod and/or plate.

Pelvic incidence (PI), also known as pelvisacral angle, is a fixed number for each patient, and is determined by the angle between a line perpendicular to the sacral plate at its midpoint and a line connecting the same point to the center of the bicoxofemoral axis. It is known that pelvic incidence is an important factor for managing spinal alignment. Another example is shown in FIG. 17B relating various angles at the pelvic region.

As discussed above, unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only and is not intended to limit the scope of the present invention, which is defined solely by the claims. Definitions of common terms in immunology and molecular biology can be found in The Merck Manual of Diagnosis and Therapy;[4] The Encyclopedia of Molecular Cell Biology and Molecular Medicine;[5] Molecular Biology and Biotechnology: a Comprehensive Desk Reference;[6] Immunology;[7] Janeway's Immunobiology;[8] Lewin's Genes XI;[9] Molecular Cloning: A Laboratory Manual.;[10] Basic Methods in Molecular Biology;[11] Laboratory Methods in Enzymology;[12] Current Protocols in Molecular Biology (CPMB)[13]; Current Protocols in Protein Science (CPPS);[14] and Current Protocols in Immunology (CPI)[15].

In the embodiments discussed and in any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined herein within the description of the various aspects of the invention.

Machine Learning Design of Orthopedic Implants and Methods for Using Same

Lumbar fusion is a surgical procedure for the treatment of degenerative and spinal deformities. Loss of lordosis after lumbar spine fusion can lead to positive sagittal balance with forward inclination of the trunk and adjacent segment degeneration, along with chronic or debilitating back pain. Identification and restoration of adequate lumbar lordosis for sagittal balance should be an everyday concern for the spine surgeon. However, the challenge is to determine the correct amount of lumbar lordosis that each patient requires to maintain optimal sagittal balance. The development of instrumentation to measure the patient has offered the advantage of a more accurate and more efficient diagnosis, but there is a huge need for intelligent surgical design of the outcome, including restoration of the alignment of the lumbar spine.

Figure 2A:
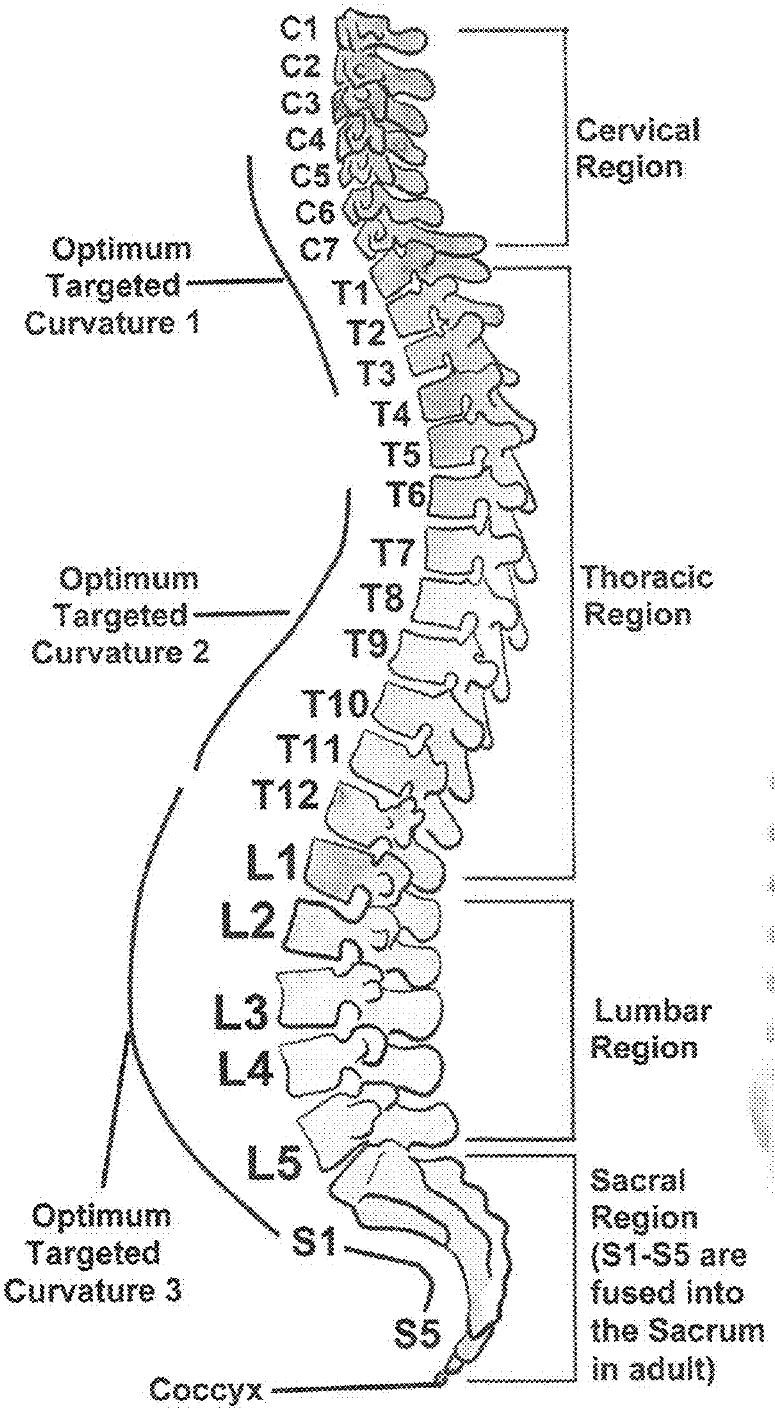
FIG. 2A shows a view of the left side of a human spine in a normal posture position (e.g., without a significant degeneration or disease) with an example optimum targeted curvature 1 (in the sagittal plane) illustrating a normal or targeted cervical-thoracic curvature, optimum targeted curvature 2 illustrating a normal targeted thoracic curvature, and optimum targeted curvature 3 illustrating a normal or targeted lumbar sacral curvature (or thoracic to lumbar curvature), without taking into consideration unique patient characteristics in this example. The vertebrae are each numbered and shown in their respective regions.
Figure 2B:
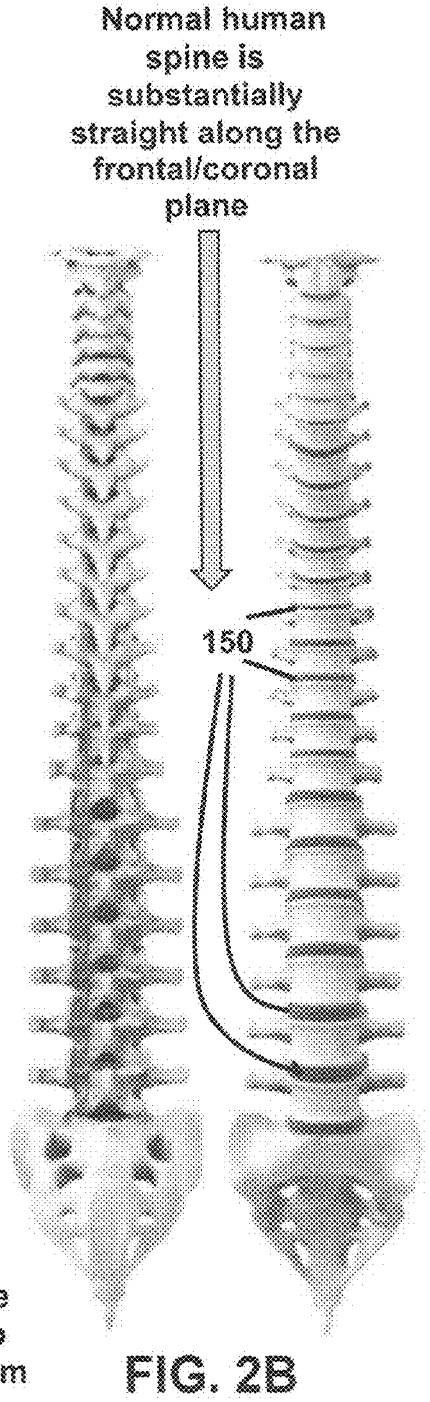
FIG. 2B shows a back view (left of the figure) of a normal (straight) human spine and a front view (right of the figure) of the normal human spine with a plurality of intervertebral discs 150 that are each indicated in examples. It is important to note that the normal human spine is significantly straight along the frontal/coronal plane when viewed from the front or back.
Figure 2D:
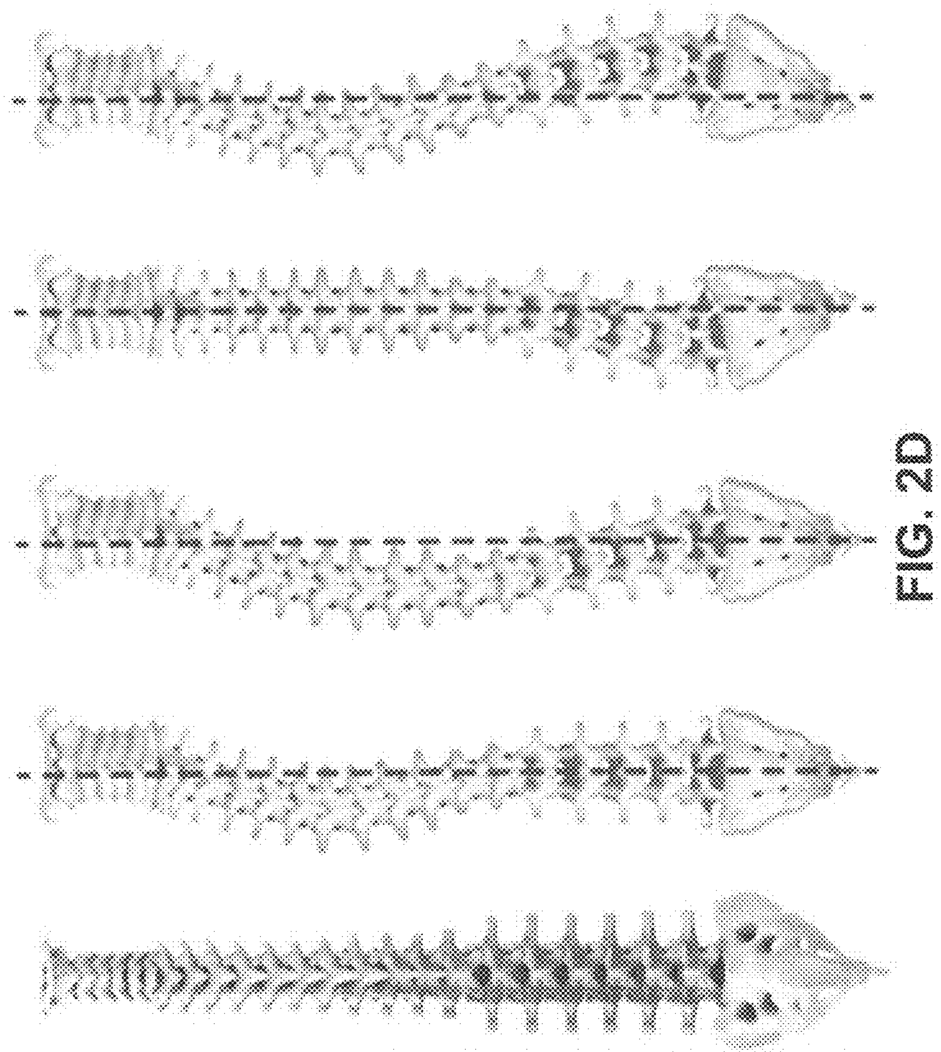
FIG. 2D shows a back view of a normal human spine (at left of the figure), a thoracic scoliosis curvature ($2^{nd}$ from left), a thoracolumbar scoliosis (center), a lumbar scoliosis ($2^{nd}$ spine from right), and a 'double curve' scoliosis spine at right.
Figure 2C:
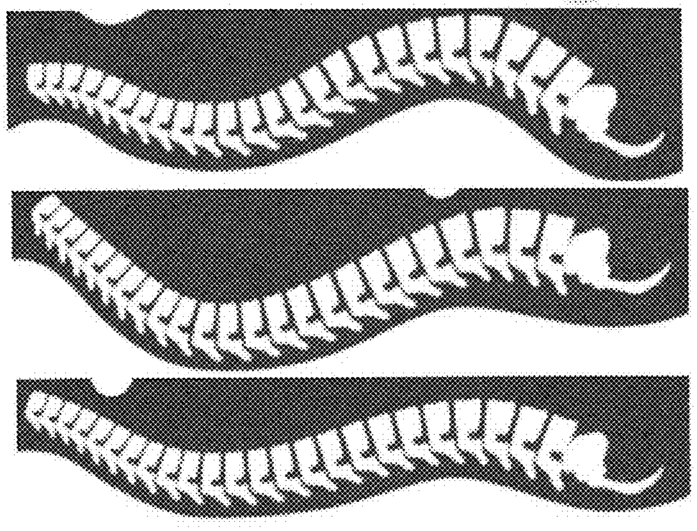
FIG. 2C shows a view of the right side of a normal human spine (at left of figure), compared to a kyphosis spine (at center of figure), and a spine with a hyper-lordosis (at the right of figure) condition.

In a broad embodiment, a huge problem in spinal surgeries is that the conventional rods (human-bent or currently manufactured worldwide) spinal rods do not meticulously follow the proper curvature of the human spine. For example, FIG. 2A shows a view of the left side of a human spine in a normal posture position (e.g., without a significant degeneration or disease) with an example optimum targeted curvature 1 (in the sagittal plane) illustrating a normal or targeted cervical-thoracic curvature, optimum targeted curvature 2 illustrating a normal targeted thoracic curvature, and optimum targeted curvature 3 illustrating a normal or targeted lumbar sacral curvature (or thoracic to lumbar curvature), without taking into consideration unique patient characteristics. In the example of FIG. 2A, for a surgeon to restore a spine with deformities (e.g., FIG. 2C or FIG. 2D), the surgeon must someone predict the shapes and sizes of the orthopedic implants in advance. After surgery, studies revealed that about 50% of spinal surgery performed produce rods that are straightened out or over-bent into an unnatural position. At first, the unfused spinal segments compensate for the improper rod contour effects, but eventually the discs above and/or below the fusion degenerate and wear down. The patient then develops back pain, has difficulty standing upright, and experiences limitations when walking. Eventually, the problem requires yet another major surgery to realign the spine. Thus, the presently disclosed technology provides machine learning in various layers of convolutional neural networks to provide pre-planned shapes, contours, curvatures, and sizes to spinal rods (and associated hardware) that enable a surgeon to plan a desired surgical outcome for the patient. This brings great relief to patients, especially over a long-term of 2 or more years.

A major problem in spinal fusion surgeries is that, over the long term of 2 or more years, the surgeons cannot predict what pelvic incidence (PI) angulation that they place the patient's spine in—it may or may not be optimal for the patient's outcome, long term. Currently, vast majority of surgeons arbitrary assign rod shapes to their spinal fusion construct without using surgical planning. Thus, the technology disclosed herein provides machine learning, convolutional neural networks, software, and intelligent methods to design implants associated with the ideal spinal shape to optimize surgical outcomes. This saves patients years of suffering and problems such as deformity.

Children provide a good example of a long-term problem that is harder to discern in adults' treatments but easy to discern in treatments of children. For some children in about the 2- to 10-year-old age range, a device known as a "growing rod" may be utilized. There are several types of growing rods including a traditional growing rod, a Vertical Expandable Prosthetic Titanium Rib (VEPTR), or a MAGnetic Expansion Control (MAGEC®) rod. The decision to use one type of device over the other depends on several things including the curve type and if there are any other underlying conditions that are contributing to, for example, a scoliosis in a child.

Another example of a traditional growing rod is a metal rod attached to the spine that is periodically lengthened by a simple procedure. It is usually attached to the spine on the top and then either attached to the spine or the hips on the bottom with the rod in between. Most often it involves two rods. The difference between this and a full spinal fusion is that there are only screws placed in the spine at the top and the bottom of the rod and not in between. This allows continued growth of the spine. In the post-operative period, there is no casting or bracing necessary and they can return to full sports after about 6 months. The rods are generally lengthened every 6-9 months depending on the age of the child. The lengthenings take place under general anesthesia. Only a small portion of the incision is used to lengthen the device.

The VEPTR device is different from the traditional growing rod in that it is attached to the ribs at the top of the device. It is then attached to the spine or the hips on the bottom. The innovation of the VEPTR provided treatment for the infant or child with a thoracic insufficiency syndrome.

The MAGEC (MAGnetic Expansion Control) device, which uses external magnets to control a rod implanted in the spine, is for children diagnosed with progressive early-onset scoliosis who have not benefited from nonsurgical treatments. The initial procedure is much like that of the traditional growing rod or VEPTR. It is attached to the ribs or the spine at the top of the device, and then attached to the spine or the hips at the bottom of the device. The initial procedure requires admission to the hospital for 3-5 days. In the post-operative period, there is no casting or bracing necessary and regular activities are not limited. The main difference between the traditional Growing Rod/VEPTR and the MAGEC is the lengthening device in the middle. In the VEPTR or traditional Growing Rod, the patient must return to the operating room to have the device lengthened every 6-9 months. With the MAGEC system, the patient can have the lengthening done in the office without anesthesia. The lengthening will involve placing an external remote controller over the location of the magnet and the rod is lengthened in a matter of minutes. The patient then has an Xray done to confirm the amount of lengthening that was achieved. There is typically not any pain involved during the lengthening. The presently disclosed technology can be used in combination with any of the growing rod examples discussed above.

To solve the problems discussed above, in some embodiments, FIG. 1 of the present technology provides an example method 100 of treating a subject in need of a spinal surgery includes receiving data 105 representing a surgical assessment of a subject, receiving data 110 indicative of the subject's spine, receiving data 115 indicative of the subject's tissues associated with the spine, and receiving data 120 indicative of the subject's tissues surrounding the spine. Process 100 superimposes 125 a shape of a rod with the data indicative of the subject's spine, the subject's tissues associated with the spine, and the subject's tissues surrounding the spine. Process 100 adjusts 130 the shape of the rod to achieve a surgical outcome of implanting the rod into the subject's spine. Any of the steps can be omitted as need or combined with other methods disclosed herein.

In some embodiments, the present invention is directed towards an orthopedic implant used for arthrodesis of the spine. More specifically, the implant cage design of the present invention enables redistribution of the lumbar spine lordosis (curvature) with one end plate of the cage being straight or flat and the other end plate having an angle.

The orthopedic implant of the present invention enables asymmetric gain of lumbar lordosis and possible adjustment of the shape of the lumbar spine to modify the apex of the lumbar spine based on the morphology of the pelvis and pelvic incidence measurement. The coupling between the rod shape and the implant cage design allow a robust control of the spinal shape and surgical planning.

Figure 4:
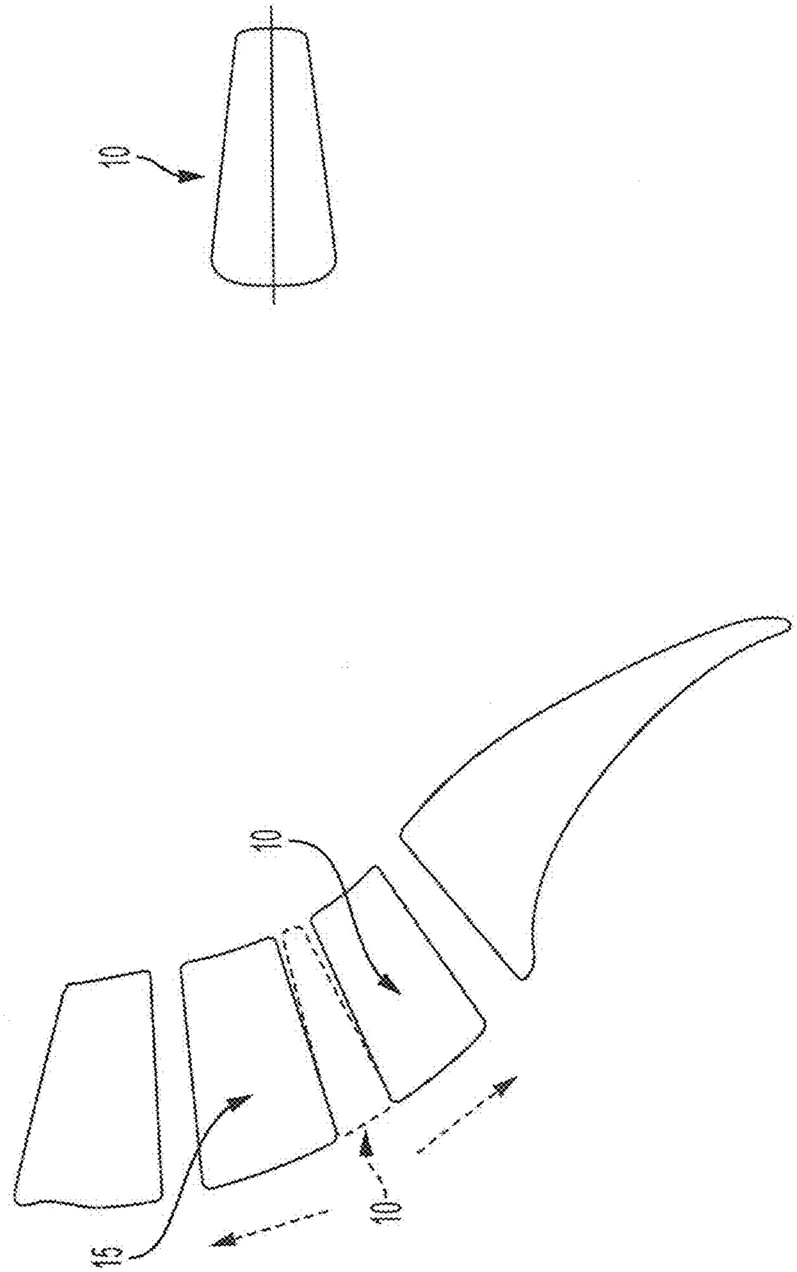
FIG. 4 (prior art) shows a diagram of flaws in cages in the market today, like implant cage 10, are symmetric in shape; two parallel end plates, two angled end plates, or a straight end plate coupled with a domed end plate (not shown). With this symmetrical slope design, a gain of the lumbar lordosis with utility of the implant cage is arbitrary and doesn't necessarily lead to a predictable shape of the lumbar spine postoperatively.

The technology herein goes beyond design of rods for a spine, as shown in FIG. 4, prior art cages in the market today, like implant cage 10, are symmetric in shape; two parallel end plates, two angled end plates, or a straight end plate coupled with a domed end plate (not shown). With this symmetrical slope design, a gain of the lumbar lordosis with utility of the implant cage is arbitrary and doesn't necessarily lead to a predictable shape of the lumbar spine postoperatively.

More specifically, when the prior art cage 10 is inserted between an upper vertebra 15 and a lower vertebra 20, the upper vertebra 15 and the lower vertebra 20 are pushed apart in opposite directions as indicated by the arrows. If multiple cages are inserted between multiple upper and lower vertebra, an apex of the lower spine changes and becomes too high.

Figure 5:
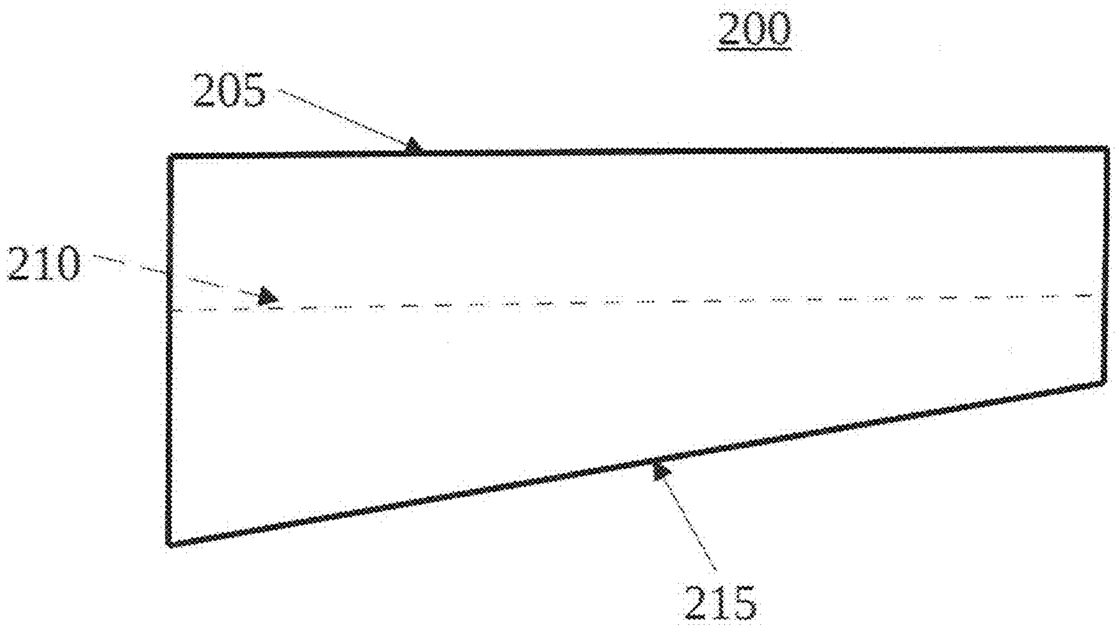
FIG. 5 illustrates an exemplary orthopedic implant cage 200 of the present invention has an asymmetric design.
Figure 6:
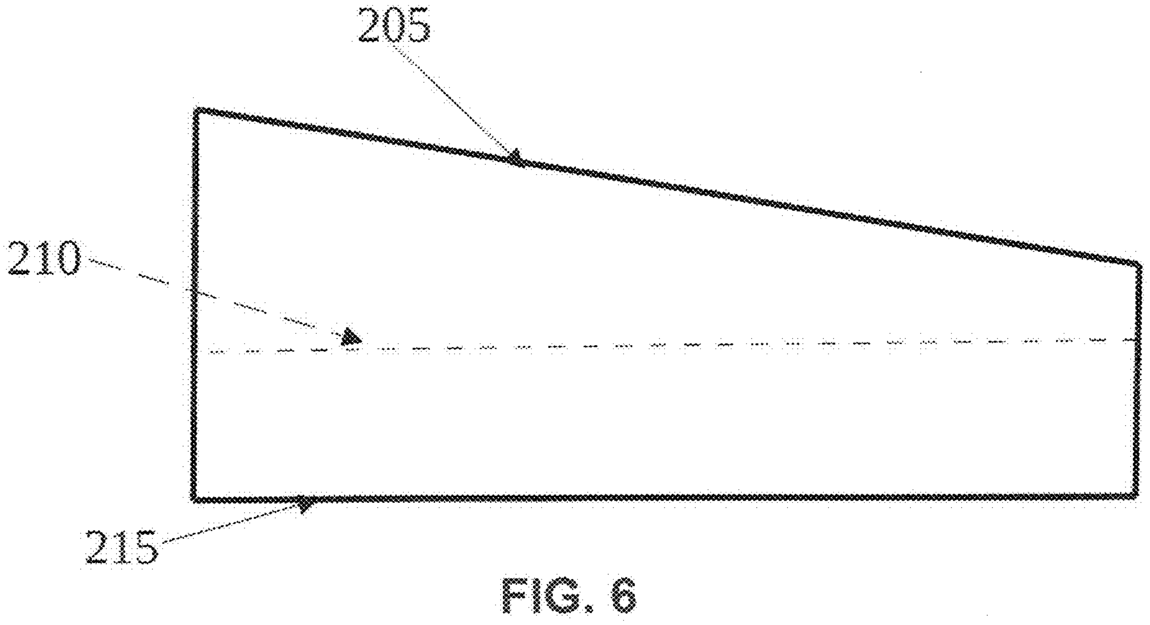
FIG. 6 shows another exemplary orthopedic implant of the present technology wherein the top portion 205 may be sloped or tapered while the bottom portion 215 is straight with respect to the center line 210.

As shown in FIG. 5, an exemplary orthopedic implant cage 200 of the present invention has an asymmetric design. More specifically, in the embodiment shown in FIG. 5, for example, a top portion 205 above the imaginary center line 210 is relatively straight with respect to a bottom portion 215 that is sloped or tapered. As will be appreciated by those of skill in this art, the slope or taper of the bottom portion 215 may be varied according to the needs of a patient and/or surgeon. Moreover, in other implementations, one of which is illustrated in FIG. 6, the top portion 205 may be sloped or tapered while the bottom portion 215 is straight with respect to the imaginary center line 210.

Figure 7:
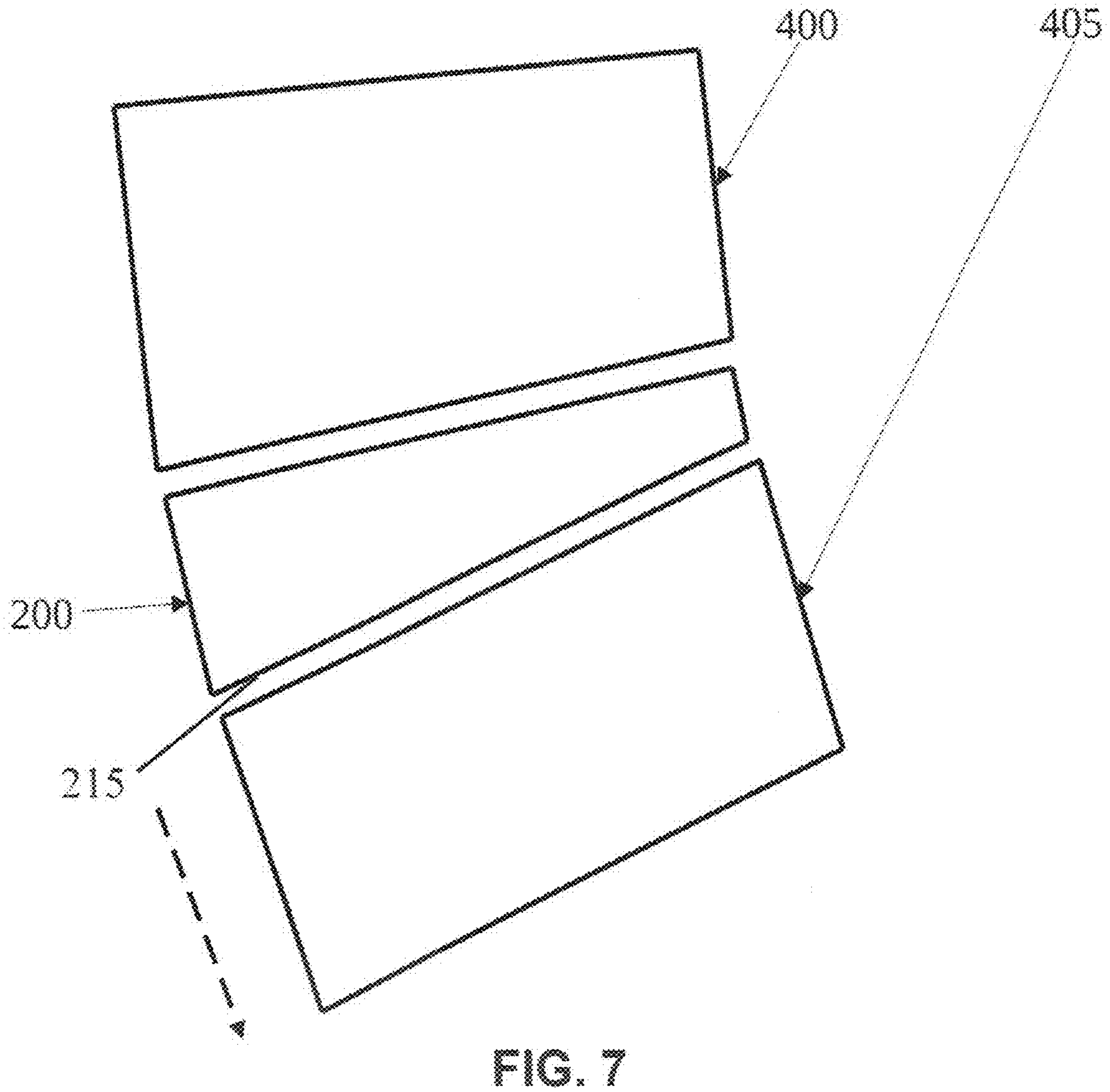
FIG. 7 illustrates how when the orthopedic implant cage 200 of the present invention is inserted between an upper vertebra 400 and a lower vertebra 405, the taper of the bottom portion 215 causes the lower vertebra 405 to move downward in a direction shown by the arrow without moving the upper vertebra 400 upward, keeping the apex of the lower spine unchanged or down.

As shown in FIG. 7, when the orthopedic implant cage 200 of the present invention is inserted between an upper vertebra 400 and a lower vertebra 405, the taper of the bottom portion 215 causes the lower vertebra 405 to move downward in a direction shown by the arrow without moving the upper vertebra 400 upward, keeping the apex of the lower spine unchanged or down. Moreover, placement, i.e., distribution, of multiple orthopedic implant cages 200 between vertebrae in the lower spine enables a surgeon to adjust a total shape of the spine.

As will be appreciated by those of ordinary skill in this art, other implementations of the asymmetric orthopedic implant cage 200 can adjust lateral insertion as well.

Figure 8:
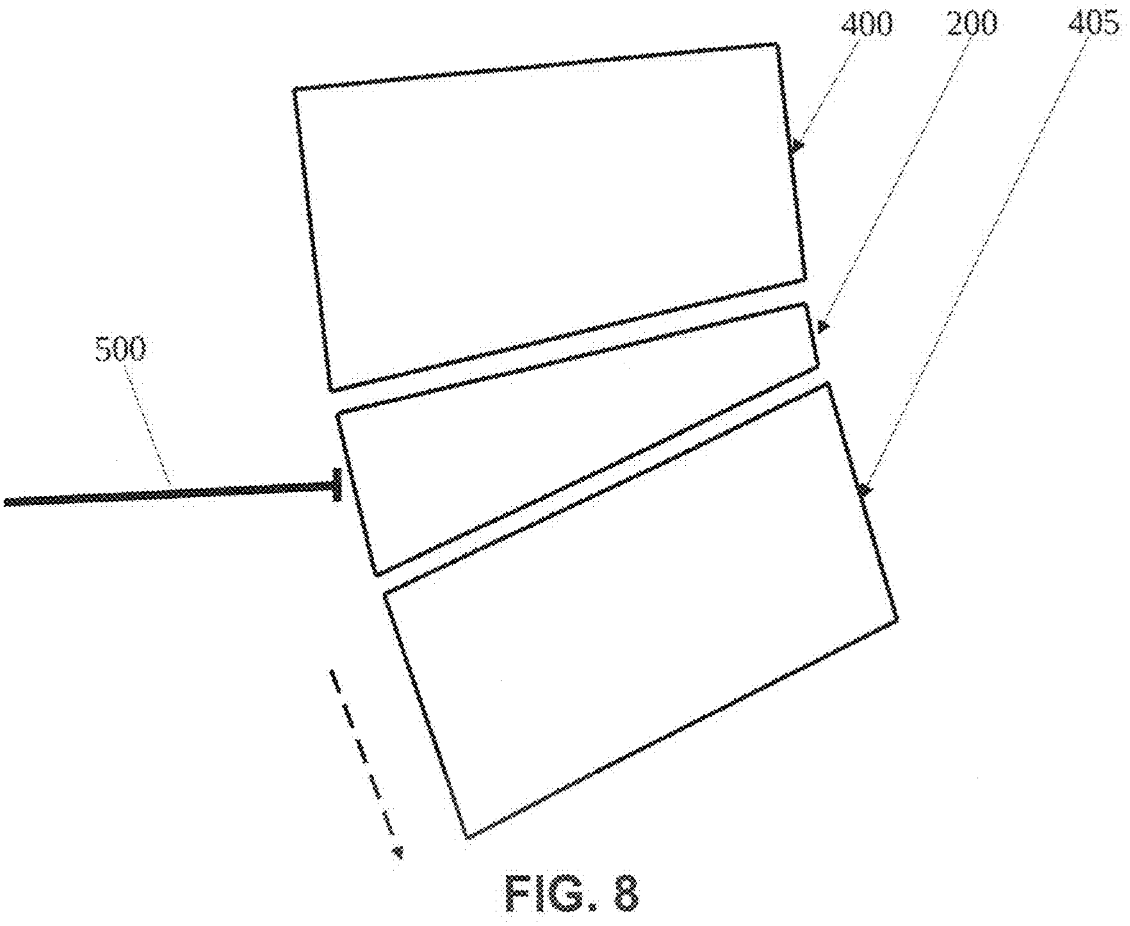
FIG. 8 illustrates how a surgeon typically uses an inserter 500 to place and push the orthopedic implant cage 200 in place. To ensure that insertion of the orthopedic implant cage 200 results in moving the lower vertebra 405 downward without moving the upper vertebra 400 upward, the inserter 500 should be placed perpendicularly to the orthopedic implant cage 200.
Figure 9:
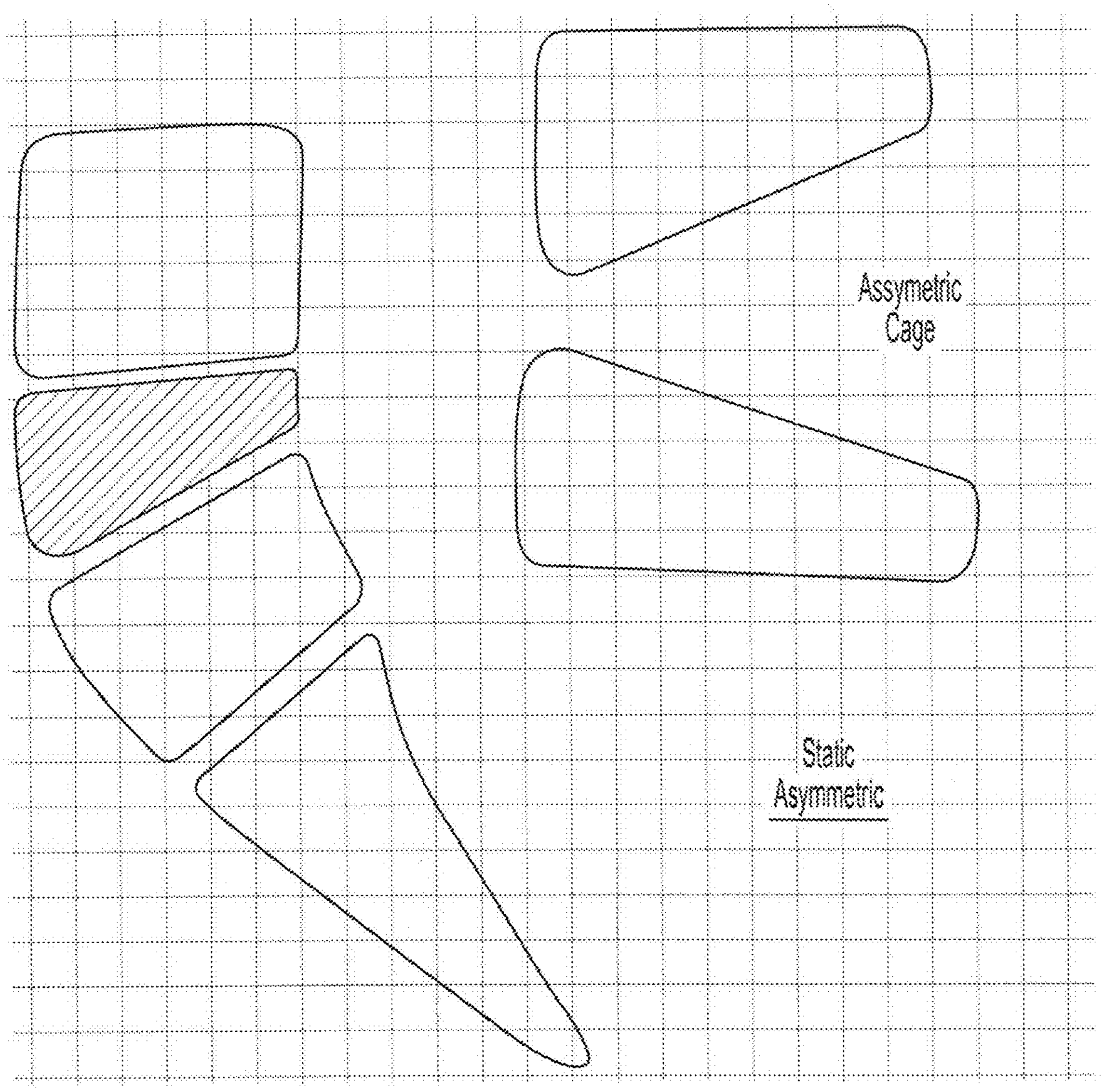
FIG. 9 illustrates an alternate embodiment of the present technology.
Figure 10:
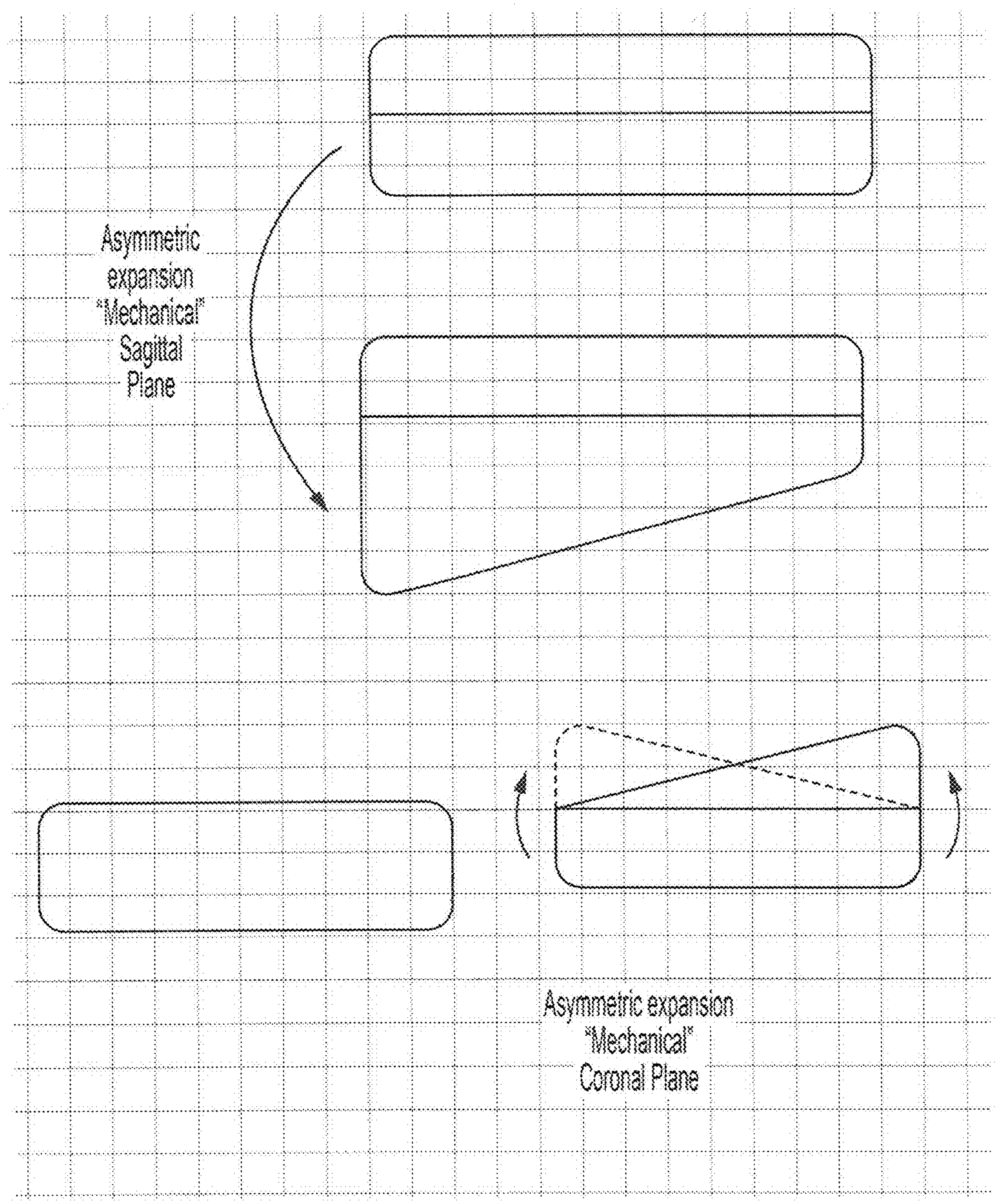
FIG. 10 illustrates an expandable implant of the present technology.

As shown in FIG. 8, a surgeon typically uses an inserter 500 to place and push the orthopedic implant cage 200 in place. To ensure that insertion of the orthopedic implant cage 200 results in moving the lower vertebra 405 downward without moving the upper vertebra 400 upward, the inserter 500 should be placed perpendicularly to the orthopedic implant cage 200.

FIG. 7, FIG. 8, FIG. 9, and FIG. 10 illustrate alternate embodiments of the interbody cages, spinal cages, and orthopedic implants of the present invention.

Figure 2E:
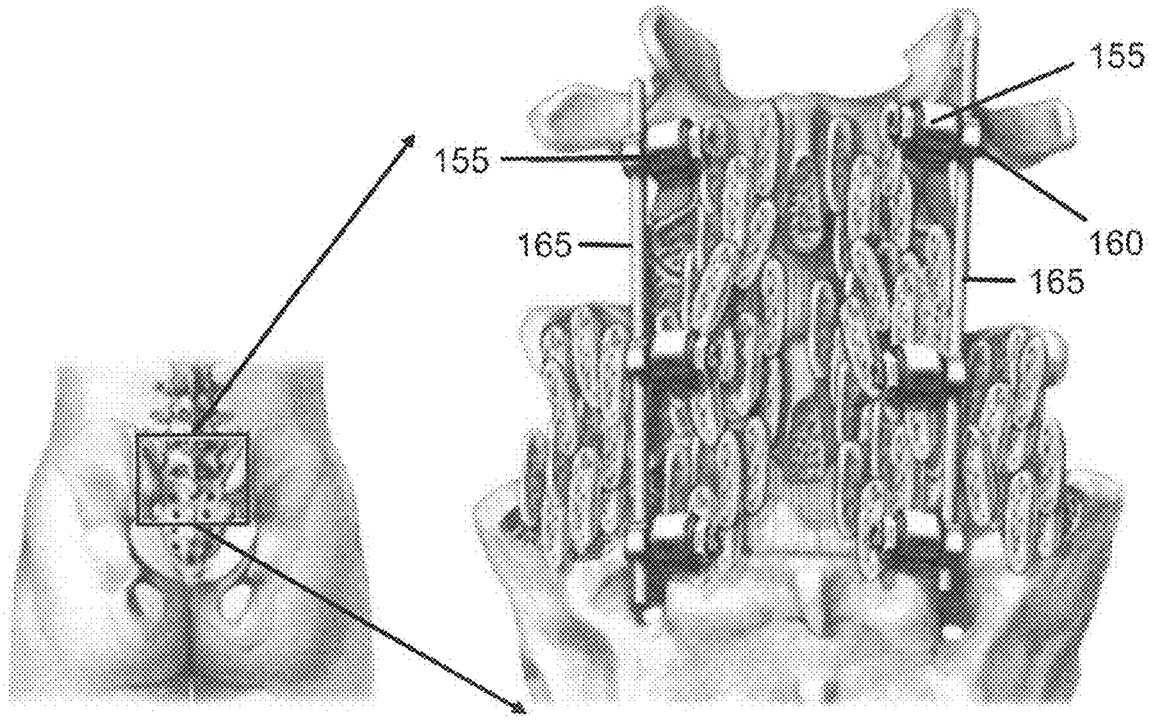
FIG. 2E (prior art[1]) shows the backside of a subject (at left of figure) and an enlarged view (at right of figure) of the subjects lumbar-sacral spine with examples of older technology spinal rods 165 (or rods), pedicle screws 160, and tulip heads 155.

Returning to the discussion of rods, currently available spinal fixation (or fusion) rods have two formats, typically—one usually used is a straight rod (e.g., FIG. 2E), and the other is a pre-bent rod. Unfortunately, the pre-bent rods are randomly bent in certain angulations, with no scientific, surgically pre-planned, or patient-specific curvature/lordosis in place. Instead, these rods have a random curvature. This complicates and compromises surgical procedures, as discussed in the problem statements above and below.

Current spinal surgical methods involving known spinal fixation rods typically include the following steps. The surgeon will take the patient to surgery and manipulate the spine via osteotomies or inner body cages. In doing so, the surgeon manipulates the patient's spine to a curvature that they feel is acceptable. The surgeon then selects a straight rod or a pre-bent fixation rod and bends it in a manner in which they think the rod will lock the patient's spine down in that curvature/desired alignment. In doing so, the surgeons do not know what pelvic incident (PI) angulation that they place the patient's spine in; it may or may not be optimal for the patient's outcome, long term, as the surgeon does not know the PI.

Pelvic incidence (PI), also known as pelvisacral angle (e.g., FIG. 17A, FIG. 17B) is a fixed number for each patient and is determined by the angle between a line perpendicular to the sacral plate at its midpoint and a line connecting the same point to the center of the bicoxofemoral axis. It is known that pelvic incidence is an important factor for managing spinal balance. As discussed in Legaye, et al., 1998,[16] (incorporated by reference herein), there is a close relationship between the anatomical parameter of pelvic incidence and the sacral slope, which strongly determines lumbar lordosis.

The fixation rods and related surgical methods discussed below provide surgeons with a more precise process by facilitating planning the surgery preoperatively, based upon the patient's pelvic incidence (PI) and figuring out what is an acceptable correction of the patient's spinal curvature based on the patient's PI. Such rods have a curvature specifically matched to a patient's pelvic incidence (PI) score. In other words, the curvature is not random, as with known pre-bent rods.

In embodiments, the orthopedic implant described above enables reshaping the spine into proper pelvic incidence (pelvic morphology) adjusted alignment. The proper pelvic incidence achieved by implantation of the implant positions the spine into a pelvic incidence angle that corresponds to spinal fixation rods. The spinal fixation rods are pre-shaped into pelvic incidence (PI) angles that correspond to the angles that will be achieved by implantation of the cage.

In embodiments, the orthopedic implant is supplemented with a pelvic incidence adjusted fixation rod that is pre-bent or prefabricated based on the morphology of the pelvis measured by pelvic incidence among other measures, such as pelvic tilt, sacral slope, and pelvic depth.

As discussed in the Examples below, appropriate rod bending based on pelvic incidence can also be achieved with machine learning software simulation (e.g., FIG. 3B, FIG. 3C, FIG. 3D, FIG. 3E, FIG. 3F, and FIG. 3G) of the orthopedic implant to achieve proper spinal alignment in both sagittal and coronal plane.

Alternatively, the correction achieved with simulation of the orthopedic implant can be planned via image processing software to generate rod shape appropriate to patient specific pelvic morphology (pelvic incidence).

FIG. 13, FIGS. 14A-14E, and FIGS. 15A-15F illustrate embodiments of the spinal fixation rods and their use with the orthopedic implant (or interbody cages) of the present invention.

According to some aspects, the solution to the problem or the inventive concept involves matching the curvature of a spinal fixation (hardware) rod that is meant for fusion of the lumbar spine, thoracic spine, or cervical spine; matching the curvature of that rod to the patient's pelvic incidence (PI) based upon preferred outcomes on segmental lordosis targets. Additionally, the rod may be matched to a patient's gender, body mass index (BMI), body habitus, and/or bone quality in various embodiments.

In embodiments, the rod may fluctuate in stiffness, shape, and materials. In embodiments, the rod made be formed from titanium alloys, cobalt-chrome alloys, or any other biocompatible, FDA-approved material. Different materials provide properties that are important for the rod's performance, including stiffness and malleability. In embodiments, a rod formed from a less stiff material is beneficial to patients that do not have great bone quality. For example, a patient with weak bones may require a less stiff material to prevent damage.

In embodiments, demarcations, markings or bands having a darker color (e.g., blue, black or purple) are formed on the rod in certain spaced locations along the length of the rod, as shown in FIG. 13 and FIGS. 14A-14E. These markings enable the surgeon to properly line the rod up to where the rod meets a pedicle screw (as dictated by the patient's anatomy) during surgery and then connect the rod to the tulip head of the pedicle screw in a very precise manner. The markings further allow the surgeon to avoid randomly or otherwise imprecisely so-called "eye-balling" or "guesstimating" the placement of the rod relative to the pedicle screw, as practiced with straight and pre-bent rods that are currently available and that have no markings on them. The markings of the inventive rods provide the surgeon an opportunity to plan where to put the rod into the tulip head of the pedicle screw, based upon the angulation of the rod. This in turn provides a very precise way to fuse a patient's vertebrae in the desired preplanned sagittal alignment.

In embodiments, markings or indicia are formed on the rod in certain spaced locations along the length of the rod to provide guidance and/or instructions to the surgeon about where to cut the rod, based on the number of spine levels being fused.

Use of the rods optimizes patient specific spinal alignment based on pelvic morphology. As described above, the markings on the rods guide the surgeon for proper predicable screw-to-rod engagement. The rods are seated in head of the screw where the markings are located.

In embodiments, the rods are matched to the patient's PI number, and the surgeon makes one or more anatomical measurements to determine the proper spinal shape in harmony with the patient morphology of the pelvis and spine.

The rods are configured to fit into the desired angulation and allow the surgeon to lock down the spine in place using pedicle screws, using the aforementioned markings.

In some embodiments, surgical planning methods include one or more of the following steps: 1. Patient sagittal (side) profile is assessed using lumbar, 36 inch or full body standing radiographs; pelvic incidence is measured based on Duval Beaupere[16] (i.e., Legaye et al., discussed above and incorporated by reference herein); radiographs are loaded on proprietary surgical planning software to generate the appropriate spine shape based on specific segmental lordosis targets based on pelvic incidence. Those targets are assigned by level of intervention and pelvic incidence value. Rod contour as well as interbody devices size, lordosis, and height is planned to fit the new alignment/contour/shape of the spine; a data-driven, artificial-intelligence, and/or machine-learning process is utilized to determine tulip head positions on the rod to ensure perfect execution of the surgical plan following the established rod contour.

Planning the tulip head offset from the vertebral body is also data driven based on proprietary data set generated from patients with significant improvement of their alignment, patient reported outcomes and have no revision surgery at 2 years follow up. Screw trajectory as well as tulip/rod intersection can be planned using navigation, robotic assistance or ultrasound guidance. Intraoperative verification of the plan includes measuring segmental lordosis and offset from assigned targets using fluoroscopy, phone, CT or ultrasound.

Reference is made to Table 1 below. The segmental lordosis values mentioned in the table are used in connection with segmental and sequential rod bending to generate full lumbar rods that are contoured based on ideal lumbar lordosis for the patient based on their pelvic incidence. The rods were then smoothed using AI driven superimposition of the segmental contouring mentioned with contours of rods utilized in patients with successful lumbar fusion. The result is a set of six pelvic incidence rods (PI-Rods) (i.e., rods having PI Categories that cover pelvic incidence angulations of <40, 40-50, 50-60, 60-70, 70-80, and >80 degrees). FIG. 15A, FIG. 15B, FIG. 15C, FIG. 15D, FIG. 15E, and FIG. 15F show examples of these six rods.

These PI rods are chosen and utilized by the surgeon to ensure achieving proper segmental lordosis targets intraoperatively. Sets of such rods may be included in a kit in various embodiments.

TABLE 1

Average Segmental Sagittal Alignment Values for the Lumbar and Thoracolumbar Spinal Regions. This table should be interpreted with caution as the values are averges and thus may not be prescriptive for every patient.

| PI Category | T10-L2 | L1-L2 | L2-L3 | L3-L4 | L4-L5 | L5-S1 |
|---|---|---|---|---|---|---|
| 40 | −6.9 | 1.7 | 4.4 | 9.5 | 15 | 17.5 |
| 50 | −4.3 | 1.7 | 6.2 | 10.1 | 15 | 20 |
| 60 | −4.3 | 3.1 | 7.9 | 11.2 | 15 | 20 |
| 70 | 2.1 | 4.9 | 9.2 | 15.4 | 15 | 20 |
| 80 | 2.1 | 5.5 | 11.9 | 17 | 19 | 20 |
| 90 | 2.1 | 7.3 | 14.6 | 12.9 | 22 | 20 |

In embodiments, the rods are configured to factor screw head position against the vertebra to generate the offset of rod distance from the spine by pelvic incidence. The rods are generated by proprietary superimposition between the shapes of the rods derived from clinical data versus those generated by our pelvic incidence adjusted rod designs.

Figure 17A:
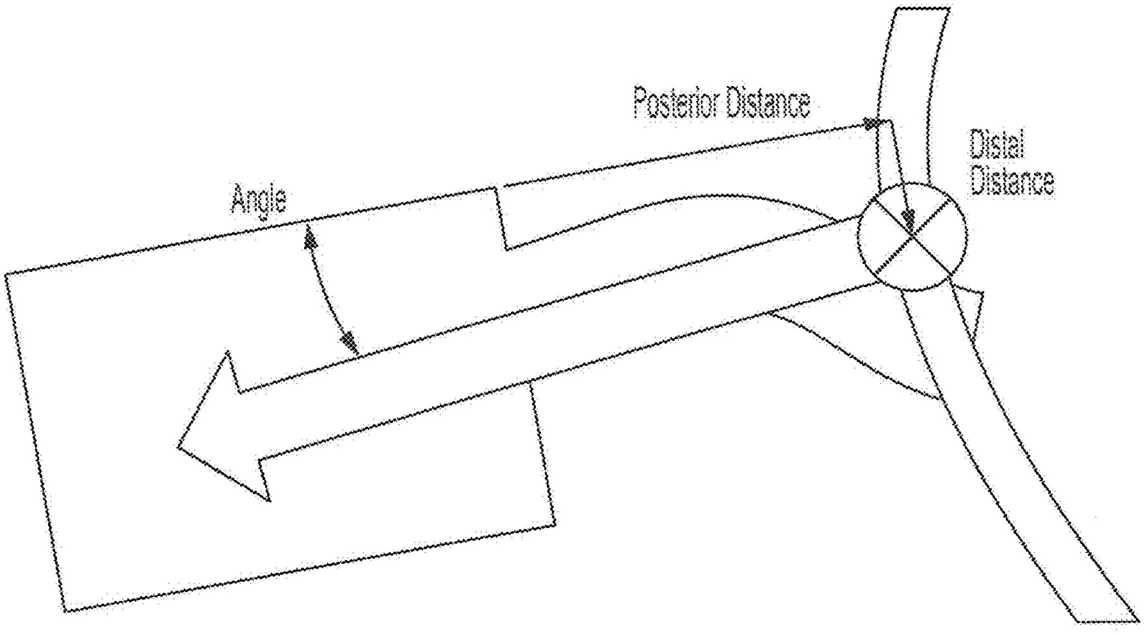
FIG. 17A shows three parameters that can be used to identify the intersection point of the tulip head of the pedicle screw and the rod, namely: angulation superior endplate versus screw (positive: screw aiming down; negative: screw aiming up); posterior offset between postero-superior corner and screw head (parallel to superior endplate) in mm; and distal offset between postero-superior corner and screw head (perpendicular to superior endplate) in mm.
Figure 17B:
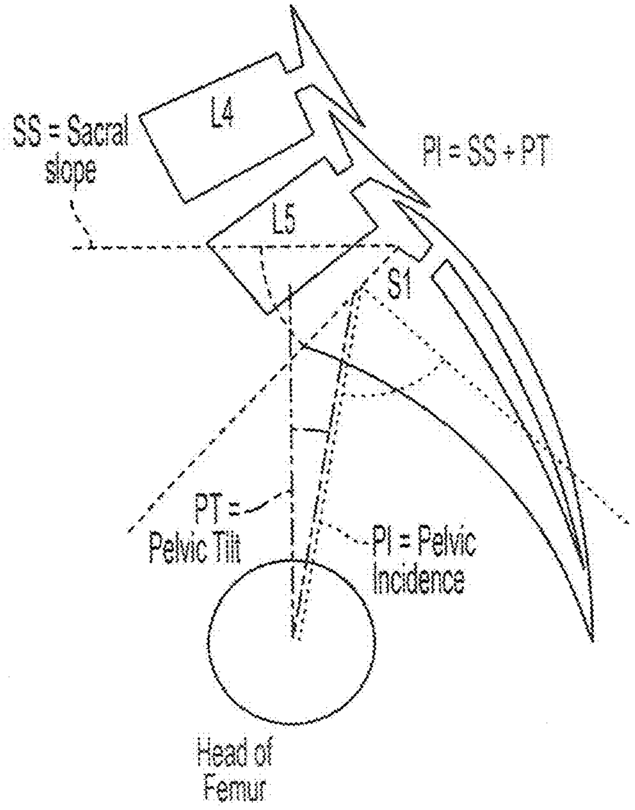
FIG. 17B shows an illustration used in some embodiments to define sacral slope (SS), pelvic tilt (PT), and pelvic incidence, along with relations among these (e.g., PI=SS+PT).

Referring now to FIG. 17A, three parameters are used to identify the intersection point of the tulip head of the pedicle screw and the rod, namely:

Angulation superior endplate versus screw (positive: screw aiming down; negative: screw aiming up).

Posterior offset between postero-superior corner and screw head (parallel to superior endplate) in mm.

Distal offset between postero-superior corner and screw head (perpendicular to superior endplate) in mm.

It would be appreciated by those skilled in the art that various changes and modifications can be made to the illustrated embodiments without departing from the spirit of the present invention. All such modifications and changes are intended to be within the scope of the present invention except as limited by the scope of the appended claims.

The invention is not limited to the embodiments hereinbefore described, which may be varied in their construction, dimensions and other structural and material details.

Modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, “each” refers to each member of a set or each member of a subset of a set.

Other embodiments of the invention will be apparent to those skilled in the art from consideration of the specification and practice of the invention disclosed herein. Although specific advantages have been enumerated above, various embodiments may include some, none, or all of the enumerated advantages. It is intended that the embodiments described above be considered as exemplary only, with a true scope and spirit of the invention being indicated by the appended claims. Moreover, none of the features disclosed in this specification should be construed as essential elements, and therefore, no disclosed features should be construed as being part of the claimed invention unless the features are specifically recited in the claims. In addition, it should be understood that any of the features disclosed on any particular embodiment may be incorporated in whole or in part on any of the other disclosed embodiments.

According to some aspects, a spinal fixation rod with an established shape, curvature, and/or contour for use in a spinal surgery on a subject’s spine is disclosed herein, the rod comprising: a curvature, shape, or a contour that is matched to at least 3 of A,B,C, and D; A) to match a unique curvature of the subject’s spine; B) to match a preferred outcome from a data set of improved patients; C) to match a machine learning algorithm for two or more tulip head screw position markings on the rod operative to ensure an execution of a surgical plan following the rod’s established contour; D) to match at least one of: the subject’s pelvic incidence (PI); the subject’s vertebrae position(s); the subject’s gender, size, body mass index (BMI), body habitus, age, and/or bone quality; and a diameter and/or a length of the rod; and wherein the rod is configured as a surgical implant ready for use by a surgeon in a surgical procedure to connect and/or contact two or more bones in the spine of the subject.

In some embodiments, the spinal fixation rod is further comprising markings in two or more spaced locations along a length of the rod, the markings configured to enable a precise alignment of the rod with a tulip head of a pedicle screw during a spinal surgery.

According to some aspects, the spinal fixation rod is wherein each of the locations of the two or more markings is operative to match the unique subject's spinal curvature, PI, and/or vertebrae position(s) because the rod is made using data from the patient's spine and surrounding tissue and an algorithm.

In some embodiments, the algorithm is executed on a processor or computer with memory, is a software-based algorithm, and/or a machine learning algorithm.

According to some aspects, the machine learning algorithm has been previously trained and/or conditioned using a data set of patients' data.

In some embodiments, the spinal fixation rod is wherein the rod is matched to a curvature of a lumbar spine, thoracic spine, and/or cervical spine region in the subject.

According to some aspects, the spinal fixation rod is wherein the rod is matched with a curvature of the rod to the subject's PI based upon a preferred outcome on a segmental lordosis target.

In some embodiments the spinal fixation rod is configured wherein the rod is matched to a preferred outcome by comparing the rod to actual data from successful implants in two or more iterative adjustments of the curvature of the rod.

According to some aspects, the spinal fixation rod is further comprising the rod is matched to the subject's gender, BMI, body habitus, and/or bone quality.

According to some aspects, the spinal fixation rod is wherein the rod comprises a growing spinal rod. In some embodiments, the spinal fixation rod is wherein the rod is a growing spinal rod capable of one or more magnetic adjustments including a magnetic expansion control. In this example, the spinal fixation rod can be further comprising one or more magnets and a motor inside the rod that enable the rod to extend. The spinal fixation can be further comprising a remote control used outside of the body operative to engage the magnets within the rod to move the rod.

According to some aspects, the spinal fixation rod is further comprising markings or indicia formed on the rod in certain spaced locations along the length of the rod to provide guidance and/or instructions to a surgeon about where to cut the rod before or during a surgery, based on the number of spine levels being fused.

In some embodiments, the rod is further comprising a designed stiffness, malleability, shape, and/or custom materials.

According to some aspects, the spinal fixation rod is wherein one or more properties of the rod include a less stiff material that is beneficial to subjects that do not have a strong bone quality or weak bones, and the less stiff material is operative to prevent damage to the bones.

In some embodiments, the spinal fixation rod is comprising titanium alloys, cobalt-chrome alloys, or a biocompatible, health authority-approved or FDA-approved material.

According to some aspects, the spinal fixation rod is, further comprising an interbody spinal cage, comprising: a singular, asymmetric frame having anterior and posterior portions, superior and inferior surfaces, and two opposing sides, the superior and inferior surfaces asymmetric with respect to a center line passing through the opposing sides.

In some embodiments, the spinal fixation rod is wherein the inferior surface of the interbody spinal cage is tapered with respect to the center line and the superior surface is parallel to the center line.

According to some aspects, the spinal fixation rod is wherein the superior surface of the interbody cage is tapered with respect to the center line and the inferior surface is parallel to the center line.

In some embodiments, the spinal fixation rod is wherein the curvature of the rod dictates the shape of the interbody spinal cage during a design of the cage.

In some embodiments, the spinal fixation rod of any configuration herein can be wherein a desired outcome PI is achieved with a software simulation of the spinal fixation rod and/or the interbody spinal cage to achieve a proper spinal alignment. The proper spinal alignment can include a sagittal and/or a coronal plane alignment.

In some embodiments, the spinal fixation rod is wherein a desired PI is achieved with image processing software to generate a rod shape appropriate to patient specific pelvic morphology and/or PI.

A kit comprising any rod disclosed herein is provided, wherein the kit is provided in an online orderable configuration, a custom kit based upon input data, or an off the shelf purchasable configuration. The kit can be further comprising instructions for use, a set of rods, or a combination thereof. In any of the embodiments disclosed herein, the rod can be configured as a plate or other shaped implant.

In some embodiments, a method of making a spinal fixation rod for use in surgery on a subject's spine is provided herein, the method comprising the steps of: (1) forming, bending, or synthesizing the rod in a curvature, shape, or a contour that is matched to at least 3 of A,B,C, and D: A) to match a unique curvature of the subject's spine; B) to match a preferred outcome from a data set of improved patients; C) to match a machine learning algorithm for two or more tulip head screw position markings on the rod operative to ensure an execution of a surgical plan following the rod's established contour; D) to match at least one of: the subject's pelvic incidence (PI); the subject's vertebrae position(s); the subject's gender, size, body mass index (BMI), body habitus, age, and/or bone quality; and a diameter and/or a length of the rod; and (2) configuring the rod as a surgical implant for use by a surgeon in a surgical procedure to connect and/or contact two or more bones in the spine of the subject.

The method can be executed at any point wherein the synthesizing comprises a 3D-printing. The method can be further comprising making one or more iterative adjustments of the rod.

According to some aspects, the method is further comprising comparing a shape of the rod to actual data from successful spinal implants.

In some embodiments, the method is further comprising implementing a table of PI values cross-referenced with average segmental spinal alignment values to generate rod shapes that are contoured to achieve an ideal spine shape in the subject.

According to some aspects, the method is wherein the segmental spinal alignment values are for lumbar and/or thoracolumbar spinal regions, and wherein segmental values in the table are used in connection with segmental and sequential rod bending to generate full lumbar rods that are contoured based on ideal lumbar lordosis for the subject based on the subject's PI.

In some embodiments, the method is further comprising the rods are smoothed using artificial intelligence (AI) or machine learning driven superimposition of the segmental contouring with contours of rods utilized in patients with successful lumbar fusion.

According to some aspects, the method is further comprising the method generates one or more rods having PI categories that will provide for a variance in a subject's PI angulations. In some embodiments the method is further comprising assigning a target shape, curvature, and/or contour to the rod based on a level of intervention in the subject and/or a PI value in the subject.

According to some aspects, the method is further comprising the step of: (3) providing one or more markings on the rod for a screw placement on the rod. The screw placement can be provided with a positioning designed with a specific angulation to tie to the rod, a fluoroscopy image, a robot, a navigation plan through the rod's position in the subject, an ultrasound, a planned driving of the lordosis and/or the spine, and/or wherein the rod at least partially dictates the screw location and orientation In some embodiments, the method is further comprising the step of: (4) scanning a shape of the rod and using a software program to compare the shape to an image of the subject to determine if the rod is in an optimum shape. For example, the image of the subject can include an X-ray.

In any interpretation of the claims appended hereto, it is noted that no claims or claim elements are intended to invoke or be interpreted under 35 U.S.C. 112(f) unless the words "means for" or "step for" are explicitly used in the particular claim.

In general, any combination of disclosed features, components and methods described herein is possible. Steps of a method can be performed in any order that is physically possible.

All cited references are incorporated by reference herein. Although embodiments have been disclosed, it is not desired to be limited thereby. Rather, the scope should be determined only by the appended claims.

While various embodiments of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure. The methods, kits, formulations, and devices disclosed herein can be combined in any way into systems to address the current public health emergency.

The machine learning methods and artificial intelligence methods described herein can be implemented in any suitable computing system. The computing system can be implemented as or can include a computer device that includes a combination of hardware, software, and firmware that allows the computing device to run an applications layer or otherwise perform various processing tasks. Computing devices can include without limitation personal computers, workstations, servers, laptop computers, tablet computers, mobile devices, wireless devices, smartphones, wearable devices, embedded devices, microprocessor-based devices, microcontroller-based devices, programmable consumer electronics, mini-computers, main frame computers, and the like and combinations thereof.

Processing tasks can be carried out by one or more processors. Various types of processing technology can be used including a single processor or multiple processors, a central processing unit (CPU), multicore processors, parallel processors, or distributed processors. Additional specialized processing resources such as graphics (e.g., a graphics processing unit or GPU), video, multimedia, or mathematical processing capabilities can be provided to perform certain processing tasks. Processing tasks can be implemented with computer-executable instructions, such as application programs or other program modules, executed by the computing device. Application programs and program modules can include routines, subroutines, programs, scripts, drivers, objects, components, data structures, and the like that perform particular tasks or operate on data.

Processors can include one or more logic devices, such as small-scale integrated circuits, programmable logic arrays, programmable logic devices, masked-programmed gate arrays, field programmable gate arrays (FPGAs), application specific integrated circuits (ASICs), and complex programmable logic devices (CPLDs). Logic devices can include, without limitation, arithmetic logic blocks and operators, registers, finite state machines, multiplexers, accumulators, comparators, counters, look-up tables, gates, latches, flip-flops, input and output ports, carry in and carry out ports, and parity generators, and interconnection resources for logic blocks, logic units and logic cells.

The computing device includes memory or storage, which can be accessed by a system bus or in any other manner. Memory can store control logic, instructions, and/or data. Memory can include transitory memory, such as cache memory, random access memory (RAM), static random-access memory (SRAM), main memory, dynamic random-access memory (DRAM), block random access memory (BRAM), and memristor memory cells. Memory can include storage for firmware or microcode, such as programmable read only memory (PROM) and erasable programmable read only memory (EPROM). Memory can include non-transitory or nonvolatile or persistent memory such as read only memory (ROM), one-time programmable non-volatile memory (OTPNVM), hard disk drives, optical storage devices, compact disc drives, flash drives, floppy disk drives, magnetic tape drives, memory chips, and memristor memory cells. Non-transitory memory can be provided on a removable storage device. A computer-readable medium can include any physical medium that is capable of encoding instructions and/or storing data that can be subsequently used by a processor to implement embodiments of the systems and methods described herein. Physical media can include floppy discs, optical discs, CDs, mini-CDs, DVDs, HD-DVDs, Blu-ray discs, hard drives, tape drives, flash memory, or memory chips. Any other type of tangible, non-transitory storage that can provide instructions and/or data to a processor can be used in the systems and methods described herein.

The computing device can include one or more input/output interfaces for connecting input and output devices to various other components of the computing device. Input and output devices can include, without limitation, keyboards, mice, joysticks, microphones, cameras, webcams, displays, touchscreens, monitors, scanners, speakers, and printers. Interfaces can include universal serial bus (USB) ports, serial ports, parallel ports, game ports, and the like.

The computing device can access a network over a network connection that provides the computing device with telecommunications capabilities Network connection enables the computing device to communicate and interact with any combination of remote devices, remote networks, and remote entities via a communications link. The communications link can be any type of communication link including without limitation a wired or wireless link. For example, the network connection can allow the computing device to communicate with remote devices over a network which can be a wired and/or a wireless network, and which can include any combination of intranet, local area networks (LANs), enterprise-wide networks, medium area networks, wide area networks (WANS), virtual private networks (VPNs), the Internet, cellular networks, and the like. Control logic and/or data can be transmitted to and from the computing device via the network connection. The network connection can include a modem, a network interface (such as an Ethernet card), a communication port, a PCMCIA slot and card, or the like to enable transmission to and receipt of data via the communications link. A transceiver can include one or more devices that both transmit and receive signals, whether sharing common circuitry, housing, or a circuit boards, or whether distributed over separated circuitry, housings, or circuit boards, and can include a transmitter-receiver.

The computing device can include a browser and a display that allow a user to browse and view pages or other content served by a web server over the communications link. A web server, sever, and database can be located at the same or at different locations and can be part of the same computing device, different computing devices, or distributed across a network. A data center can be located at a remote location and accessed by the computing device over a network. The computer system can include architecture distributed over one or more networks, such as, for example, a cloud computing architecture. Cloud computing includes without limitation distributed network architectures for providing, for example, software as a service (SaaS).

The technology described herein is further illustrated by the following examples which in no way should be construed as being further limiting. The Examples are provided to demonstrate examples of future planned work, which in some experiments is emergency work. Although methods and materials similar or equivalent to those described herein can be used in the practice or testing of this disclosure, suitable methods and materials are described below.

EXAMPLES

The invention now being generally described, it will be more readily understood by reference to the following examples which are included merely for purposes of illustration of certain aspects and embodiments of the present invention and are not intended to limit the invention.

Example 1. Initiation of Automated Patient Data Interpretation, Projected with Preferred Surgical Outcomes Data sources were initially from three from different databases: 1) asymptomatic subjects were analyzed to define ideal segmental lordosis per vertebral level per pelvic incidence. Subjects with surgeries in 2) patient populations data were analyzed as well to define ideal rod shapes that corresponded with excellent patients reported outcomes and no revision/complication at follow up. A third database included 3) anatomical parameters (FIG. 3A) to define the average vertebral column shape in terms of height per level and distance of pedicle entry from the vertebral body. Using different levels of convolutional neural networks, ML/AI (machine learning/artificial intelligence was used to superimpose the 3 sources of data to generate 6 Rod categories based on patient specific morphology (e.g., pelvic incidence).

The segmental lordosis values discussed in Table 1 above were used in connection with segmental and sequential rod bending to generate full lumbar rods that are contoured based on ideal lumbar lordosis for the patient based on their pelvic incidence. The rods were then smoothed using AI driven superimposition of the segmental contouring mentioned with contours of rods utilized in patients with successful lumbar fusion. The result is a set of six pelvic incidence rods (PI-Rods) (i.e., rods having PI Categories that cover pelvic incidence angulations of <40, 40-50, 50-60, 60-70, 70-80, and >80 degrees). FIG. 15A, FIG. 15B, FIG. 15C, FIG. 15D, FIG. 15E, and FIG. 15F show examples of these six rods.

Interestingly, for patients with different PIs, the S1 distal position was different with a deeper screw for patient with a larger PI. Regarding posterior disc heights, various data from the scientific literature[17] was compared with a normative database compiled from 190 asymptomatic volunteers. The vertebra distances were significantly difference at L4 to L1. Mainly, larger PI, smaller distance, from 26 to 24 (delta 2 mm). Before implementation of software, Main parameters associated with the construction of the rod's shape were segmental angle; sisc height: normative data published; vertebra posterior height: initially simplified to 25 mm, and a point-by-point construction of the posterior wall of the spine was implemented. The mean values across entire groups were used for Rod construction (discussed for Table 1 above). Upon examination of the problems associated with the currently available technology and data from years of follow-up assessments, it was determined the present technology will have a positive impact on patients for years to come and for lifetimes of benefits. In a prophetic future example, the rods and interbody cages are implanted into actual subjects in need of customized spine surgery. Outcomes are monitored 1, 2, 3, 4, and 5 years into the future and compared with the historical databases discussed above. Further training of the machine learning algorithm is utilized, for example, as shown in the method of FIG. 3I). Next, major work was undertaken to implement automated procedures in the form of software.

Example 2. Proprietary Software Implementation Provides Real Time Visualization of Outcomes Based on Machine Learning Algorithms A surgical planning software was encoded, designed, debugged, and implemented in multiple revisions and versions. The software is a proprietary spine suite tool that allows for loading and automatic measurement of spine images to perform an in-depth analysis of the segmental, regional and global alignment of the spine.

Figure 3B:
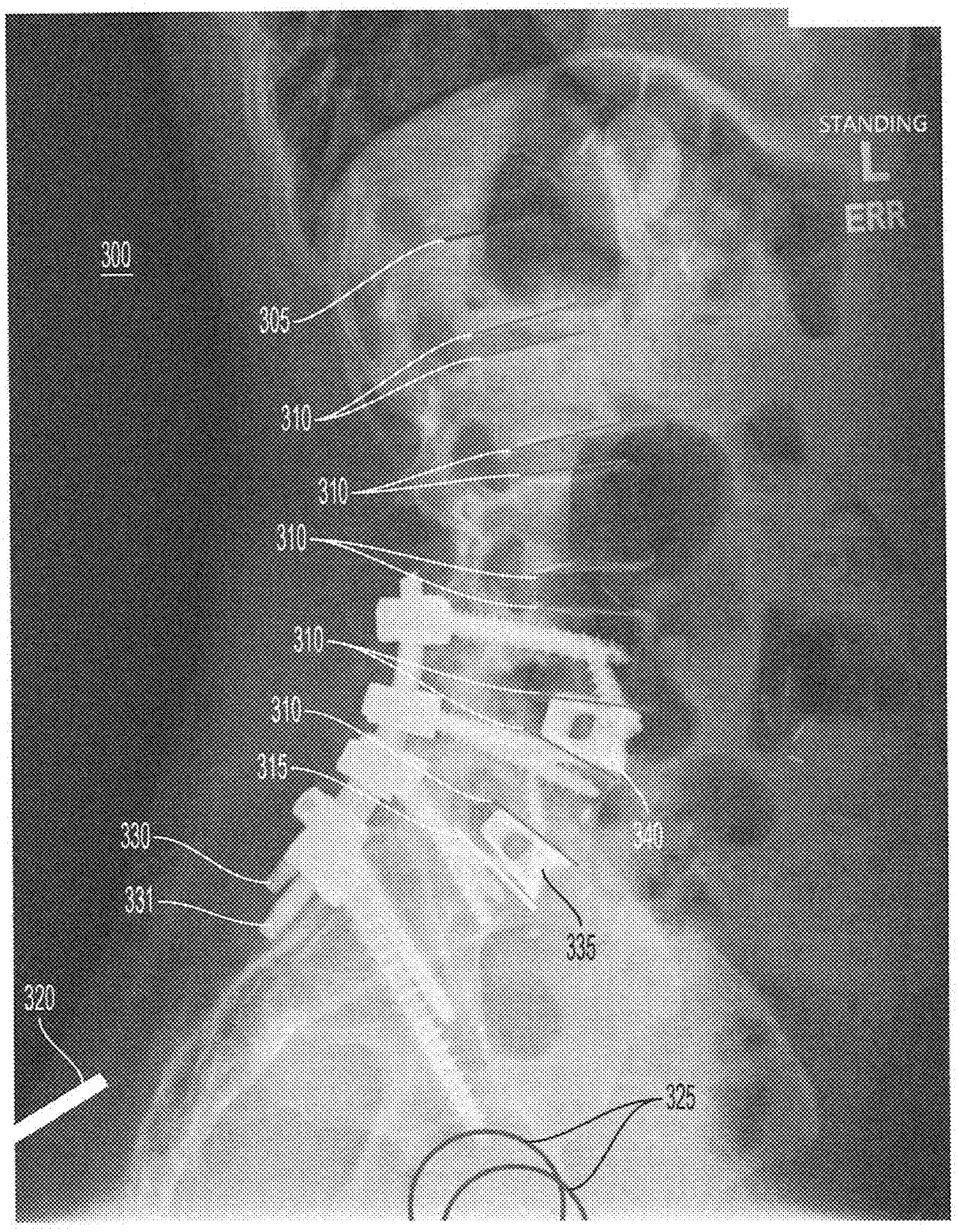
FIG. 3B shows an example of an X-ray or acquired data 300 from a subject in need of a spine surgery with a top of the L1 vertebra labeled (by proprietary automated software discussed herein) at line 305, intervertebral discs between lumbar vertebrae are labeled at a plurality of angled lines 310, and the top of the sacrum at angled line 315. The intervertebral discs are between the lines 310, which indicate the upper and lower edges of each vertebra. The pelvic incidence or angle of the sacrum is measured at 320, and the heads of the femurs (e.g., at the hip joints) on both sides of the patient are indicated at circles 325. There are shown custom spinal fusion cages 335 and 340 along with spinal rods 330 and 331.

For example, a radiograph or an X-ray (or other acquired data) is input into the software suit, and FIG. 3B shows an example of an X-ray or acquired data 300 from a subject in need of a spine surgery with a top of the L1 vertebra labeled (by the proprietary automated software discussed herein) at line 305, intervertebral discs between lumbar vertebrae are labeled at a plurality of angled lines 310, and the top of the sacrum at angled line 315. The intervertebral discs are between the lines 310, which indicate the upper and lower edges of each vertebra. The pelvic incidence or angle of the sacrum is measured at 320, and the heads of the femurs (e.g., at the hip joints) on both sides of the patient are indicated at circles 325. In this example, there are shown custom spinal fusion cages 335 and 340 along with spinal rods 330 and 331.

Figure 3C:
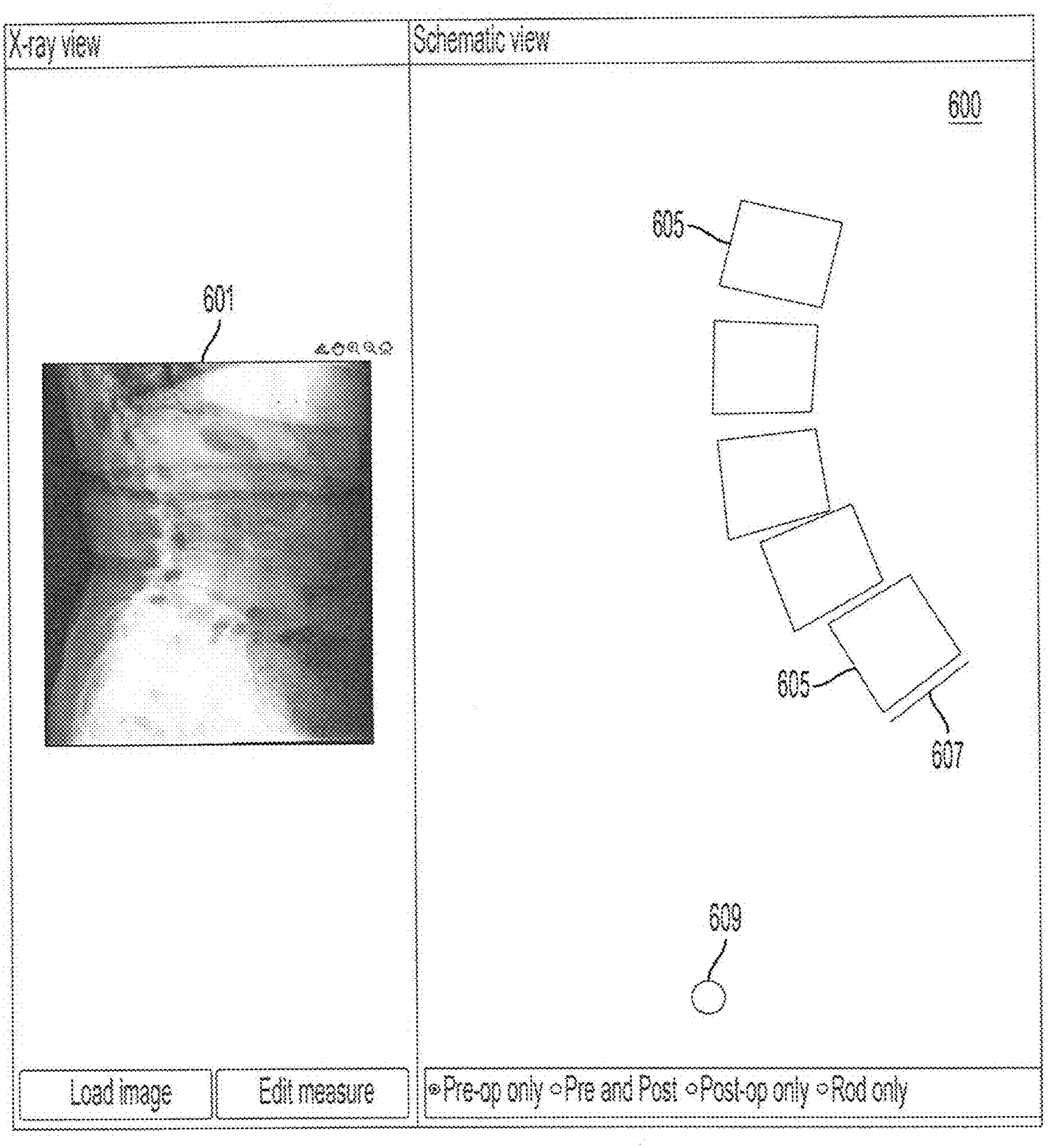
FIG. 3C shows a screenshot 600 of propriety automated software that has input patient data 601 (at left) and identified the patient's exact positions of L1-L5 at 605 and the pelvic incidence (not shown) from parameters such as the top and angle of the sacrum 607 and the position of the head of the femur or hip joint 609.
Figure 3D:
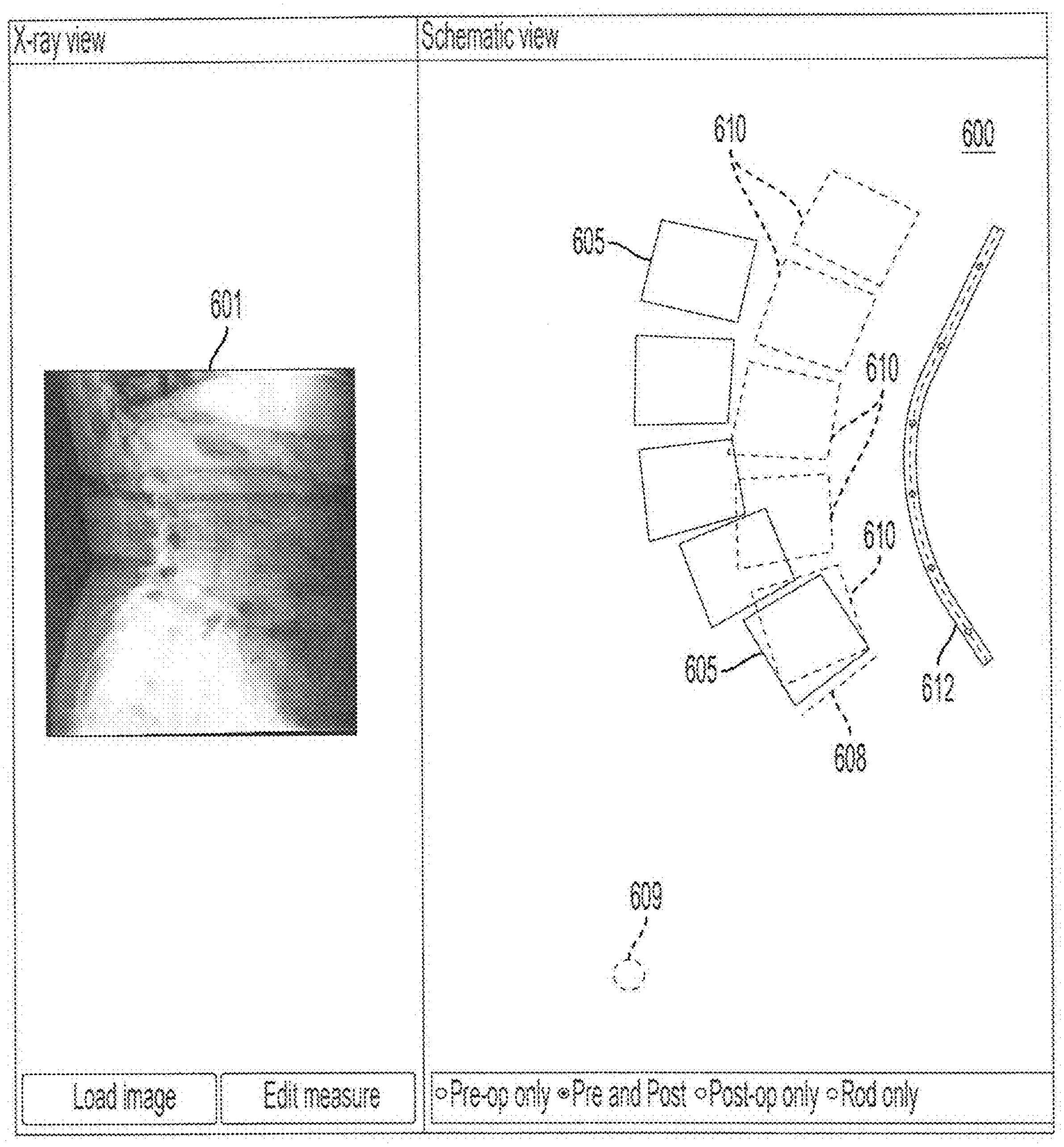
FIG. 3D shows the screenshot 600 of the example of propriety automated software from FIG. 3C that has input patient data 601 and identified the patient's exact digitalized positions of L1-L5 at 605 and the pelvic incidence (not shown) from parameters such as the (in digital formats) top and angle of the sacrum 607 (labeled in FIG. 3C) and the position of the hip joint 609. Showing more features in FIG. 3D, machine learning along with detailed parameters (not shown) have generated optimum targeted positions of the patient's L1-L5 vertebrae shown in L1-L5 pointed to by lines at 610. The optimum targeted positions are displayed on the same scale as the actual vertebrae of the patient in 605 and provide a picture of the desired surgical outcome for the patient. The propriety software has generated a shape of an optimum spinal rod and shown it at 612, and the optimum pelvic incidence is represented (and shown) by 608.

To provide a demonstration of the software, building upon the software's functions by providing more screenshots, FIG. 3C shows a screenshot 600 of the propriety automated software that has input patient data 601 (at left) and identified the patient's exact positions of L1-L5 at 605 and the pelvic incidence (not shown) from parameters such as the top and angle of the sacrum 607 and the position of the head of the femur or hip joint 609. FIG. 3D shows the screenshot 600 of the example of propriety automated software from FIG. 3C that has input patient data 601 and identified the patient's exact digitalized positions of L1-L5 at 605 and the pelvic incidence (not shown) from parameters such as the (in digital formats) top and angle of the sacrum 607 (labeled in FIG. 3C) and the position of the hip joint 609. Showing more features in FIG. 3D, machine learning along with detailed parameters have generated optimum targeted positions of the patient's L1-L5 vertebrae shown in L1-L5 pointed to by lines at 610. In this example, the optimum targeted positions are displayed on the same scale as the actual vertebrae of the patient in 605 and provide a picture of the desired surgical outcome for the patient. The targeted positions can be zoomed, rotated, and viewed at various angles to help plan the surgical outcome. The propriety software has generated a shape of an optimum spinal rod and shown it at 612, and the optimum pelvic incidence is represented (and shown) by 608.

Figure 3E:
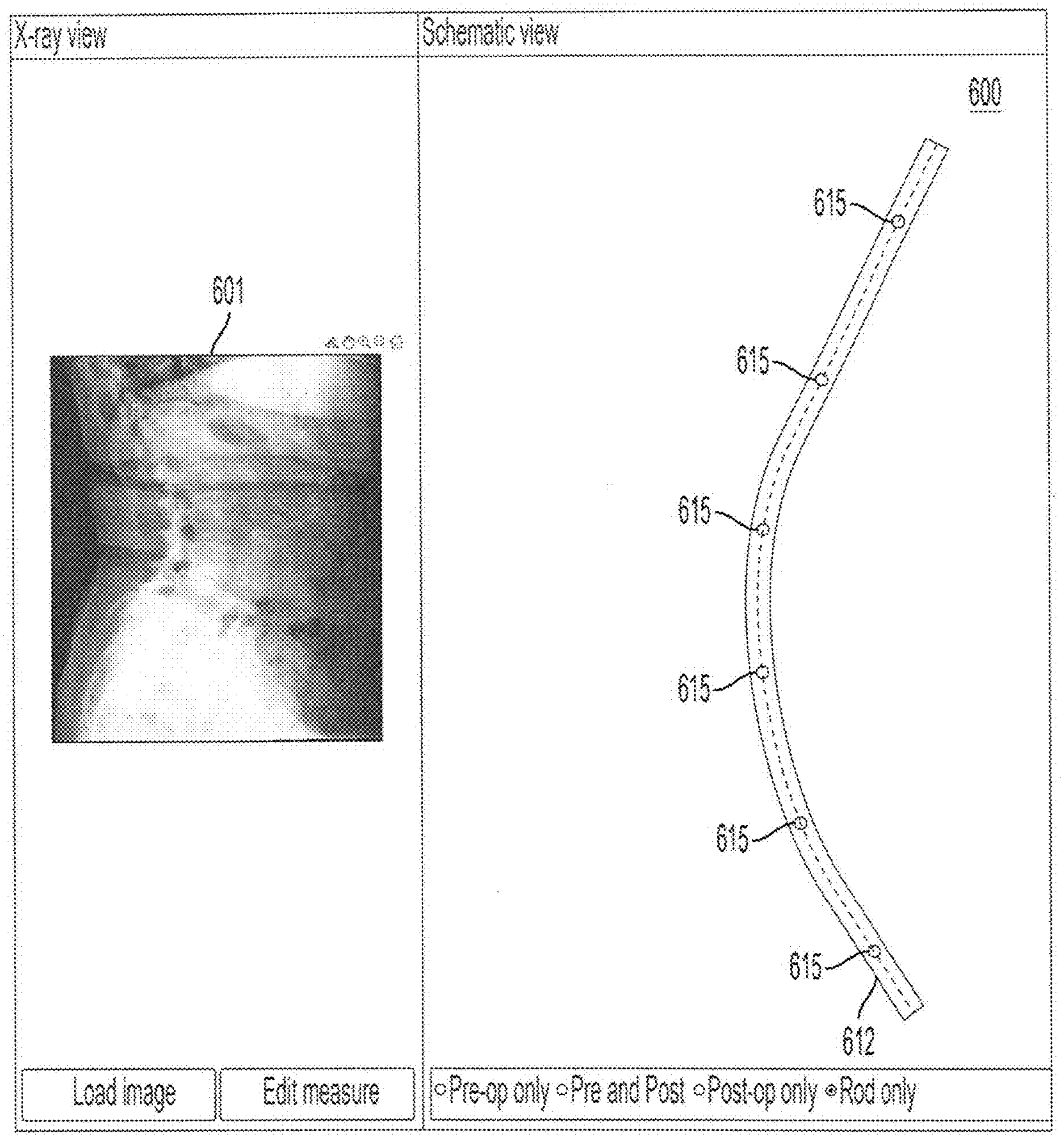
FIG. 3E shows a screenshot 600 of the propriety software that highlights the planned surgical positions of the tulip heads 615 of the pedicle screws along the rod 612. The positions 615 will provide the preferred surgical outcome for the patient over the long term after the surgery. Each of the positions 615 will be marked on the actual surgical rod to indicate to the surgeon accurate positioning of the rod (fastened into the tulip heads) during the execution of the surgery.

FIG. 3E shows a screenshot 600 of the propriety software that highlights the planned surgical positions of the tulip heads 615 of the pedicle screws along the rod 612. The positions 615 will provide the preferred surgical outcome for the patient over the long term after the surgery. Each of the positions 615 will be marked on the actual surgical rod to indicate to the surgeon proper placement of the rod (during surgery) on the tulip heads of the pedicle screws.

Figure 3F:
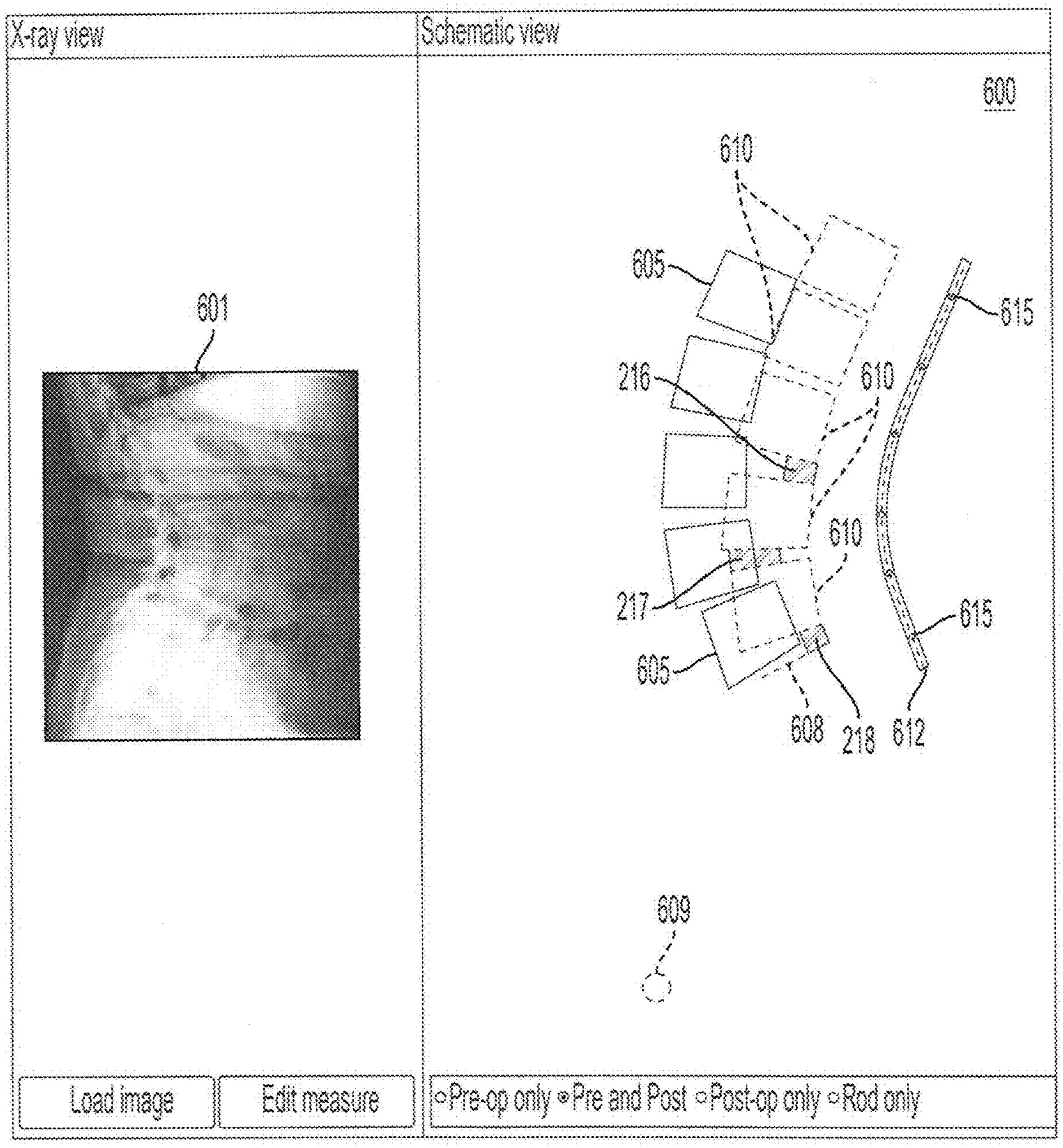
FIG. 3F shows the planned spinal rod shape 612, the planned tulip head positions 615, and the optimum L1-L5 vertebrae 610. Next, the software has calculated using trained machine learning, optimum shapes, positions, and sizes for spinal fusion cage 216, 217, and 218, with the cages tied to the entire planned surgical outcome led by the rod 612, tulip head positions 615, and the optimum vertebrae placements 610. The patient's original (problematic) vertebrae positions 605 are the same as shown in FIG. 3C and in FIG. 3D. Some numerically large details from the software have been left out in FIG. 3C, FIG. 3D, FIG. 3E, and FIG. 3F. To illustrate some more details.
Figure 3G:
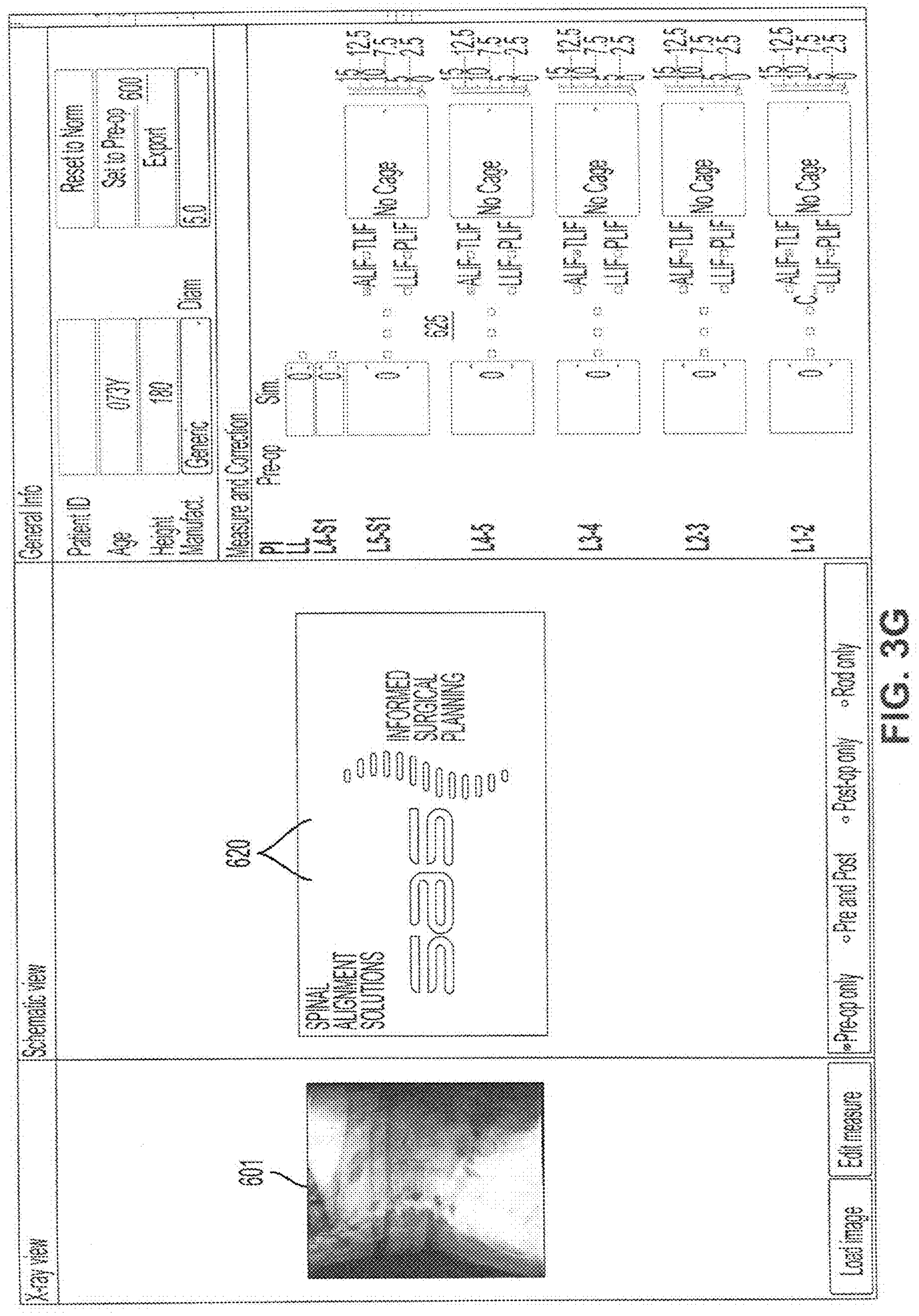
FIG. 3G shows a screenshot 600 of the software with the numeric details 625 shown for the surgeon and the proprietary software logo 620.
Figure 3H:
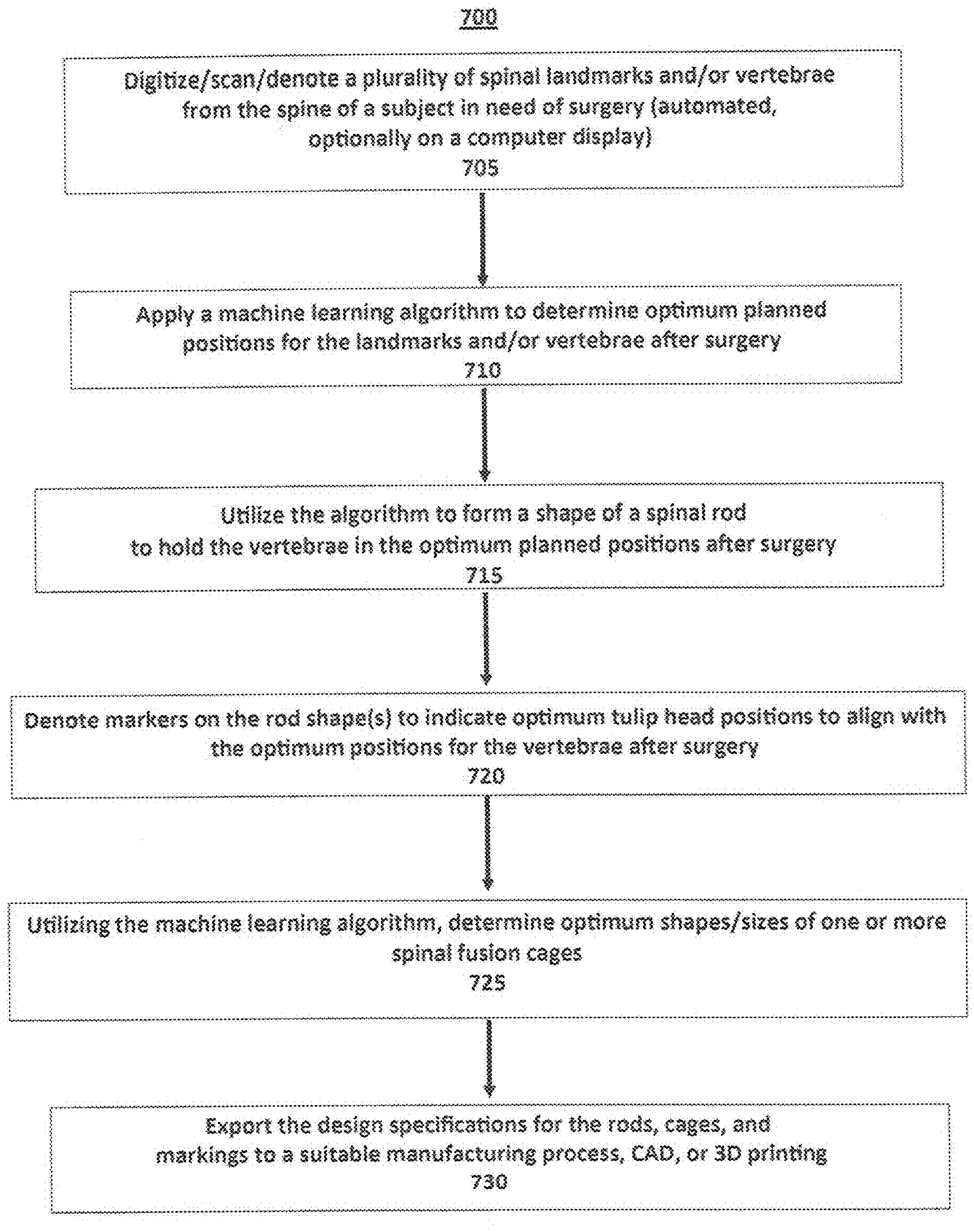
FIG. 3H shows an example method 700 for forming the rod 612, tulip head positions 615, and fusion cages 216, 217, and 218 depicted in FIG. 3F.
Figure 3I:
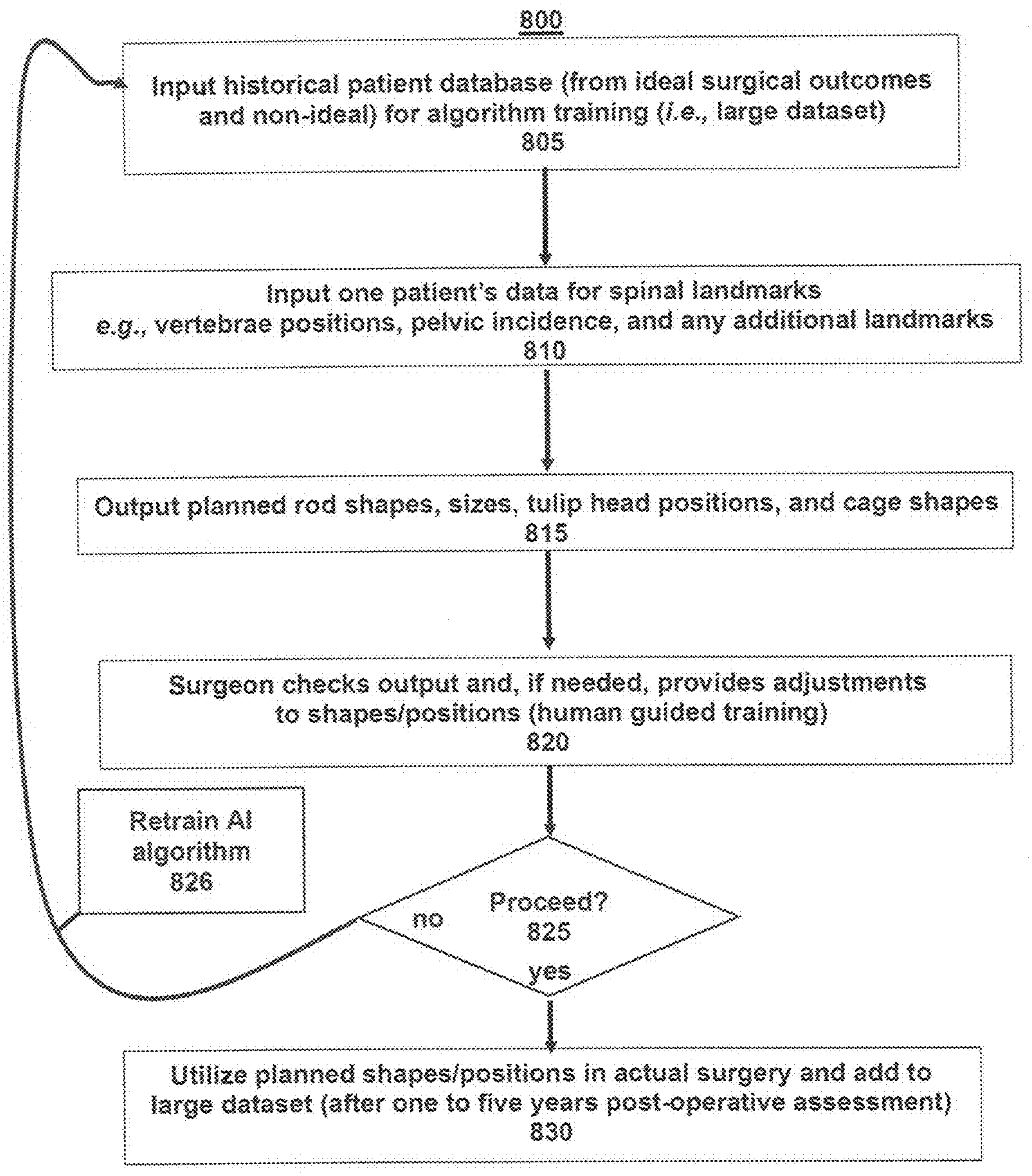
FIG. 3I shows an example method 800 for training and verifying a machine learning algorithm that is suitable for the method of FIG. 3F. utilizing exemplary human guided training at 820.

FIG. 3F shows the planned spinal rod shape 612, the planned tulip head positions 615, and the optimum L1-L5 vertebrae 610. Next, the software has calculated using trained machine learning, optimum shapes, positions, and sizes for spinal fusion cage 216, 217, and 218, with the cages tied to the entire planned surgical outcome led by the rod 612, tulip head positions 615, and the optimum vertebrae placements 610. The patient's original (problematic) vertebrae positions 605 are the same as shown in FIG. 3C and in FIG. 3D. Large details from the software have been left out in FIG. 3C, FIG. 3D, FIG. 3E, and FIG. 3F. To illustrate some more details, FIG. 3G shows a screenshot 600 of the software with the numeric details 625 shown for the surgeon and an example of the proprietary software logo 620. FIG. 3H shows an example method 700 for forming the rod 612, tulip head positions 615, and fusion cages 216, 217, and 218 depicted in FIG. 3F. FIG. 3I shows an example method 800 for training and verifying a machine learning algorithm that is suitable for the method of FIG. 3F. utilizing exemplary human guided training at 820.

During this work, a sagittal profile of the subject is assessed using lumbar, 36 inch (91.4 cm), and/or full body standing radiographs; a pelvic incidence (PI) of the subject is measured by a human or semi-automatically or fully automatically using a dedicated software with a machine learning algorithm; one or more radiographs are loaded on a surgical planning software; a rod contour is planned; an interbody device size, lordosis, and/or height is planned to fit the new alignment/contour/shape of the spine; a data-driven, artificial-intelligence, and/or machine-learning process is utilized to determine tulip head positions on the rod to ensure perfect execution of the surgical plan following the established rod contour; a tulip head offset from one or more vertebral bodies is also planned based on a data driven, proprietary data set generated from patients with significant improvement of their alignment, patient reported outcomes and have no revision surgery or mechanical complications at 2 years follow up; and a screw trajectory and/or a tulip/rod intersection is planned using free-hand, navigation, robotic assistance, and/or ultrasound guidance. The intensive data generated from populations of patients is utilized to train machine learning algorithms.

Example 3. Custom Training of the Machine Learning Algorithm and Flexible Feature Options in the Software Implementation The custom designed artificial intelligence surgical planning software is also able to automatically realign the spine into the proper shape per the patient morphology and surgeon desire. Based on surgeons' techniques and choices, the software is able to generate patient-morphology specific rods by accepting input of highly patient specific data. Examples are the subject's pelvic incidence (PI); the subject's vertebrae position(s); the subject's gender, size, body mass index (BMI), body habitus, age, and/or bone quality; and a diameter and/or a length of the rod.

Figure 16A:
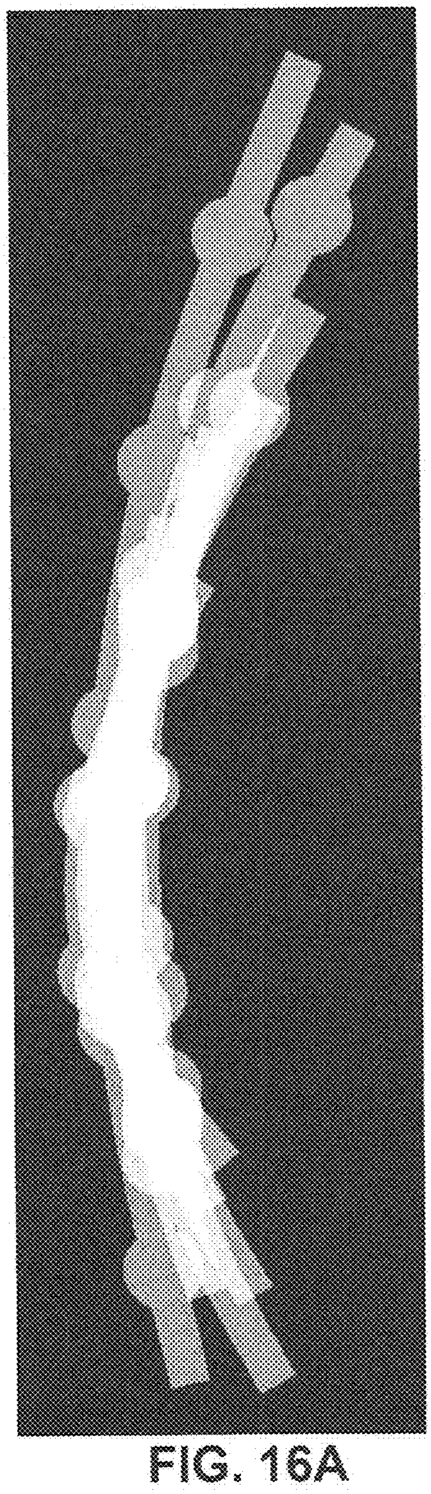
FIG. 16A shows an overlay of 7 patients' rod shapes for fusing from S1 to L3 (at least 4 vertebrae fused).
Figure 16B:
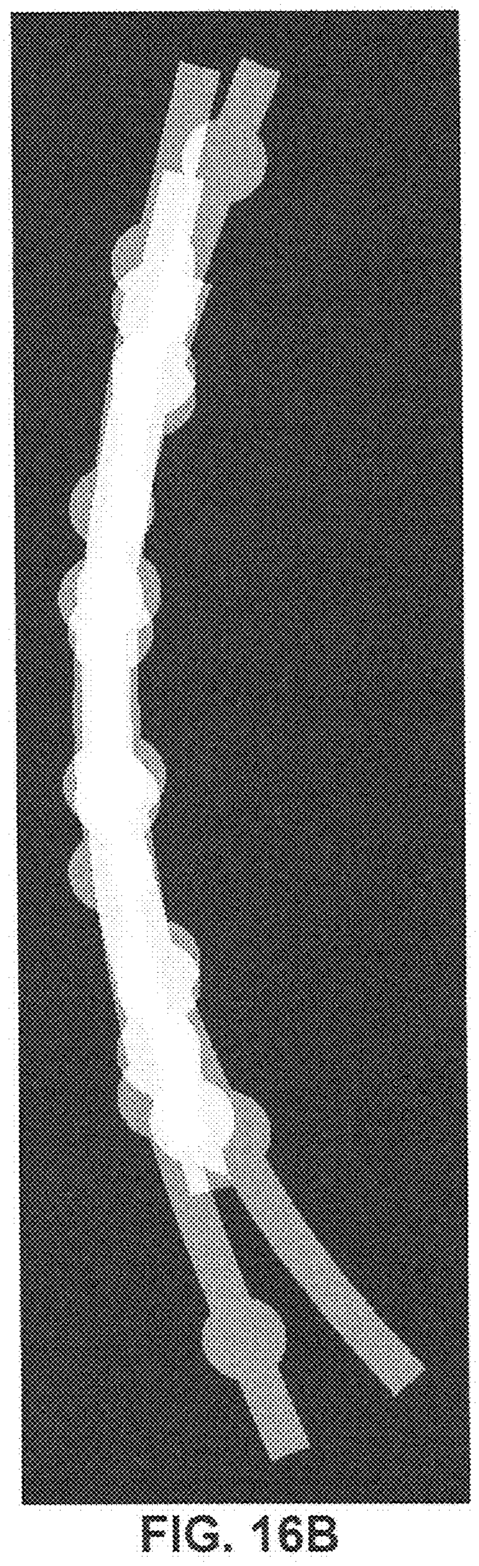
FIG. 16B shows an overlay of 4 patients' rod shapes for fusing from L5 to L2.
Figure 16C:
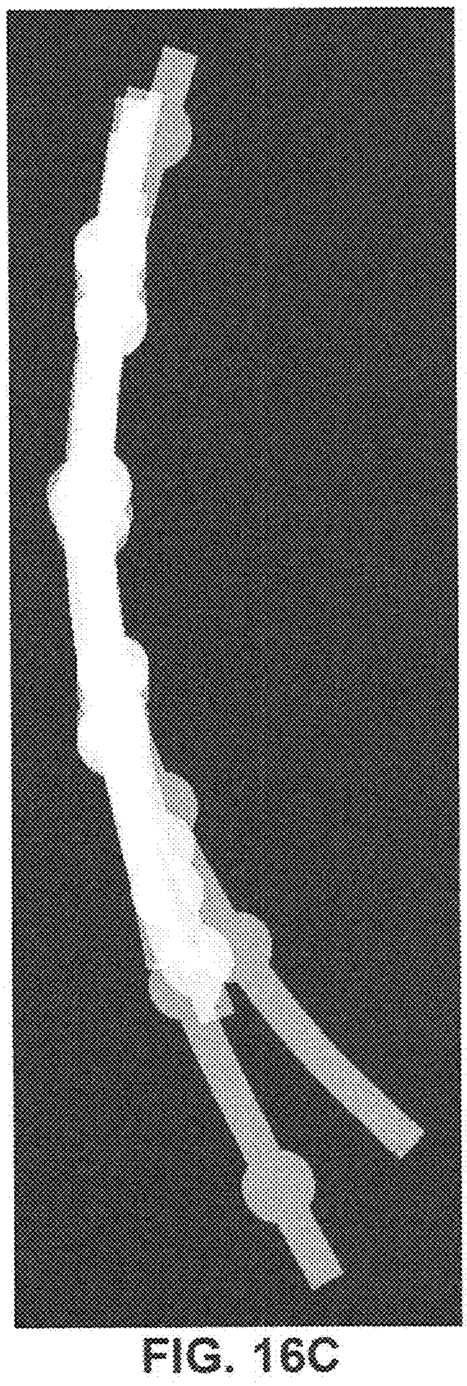
FIG. 16C shows an overlay of 6 patients' rod shapes for fusing from L4 to L2.
Figure 16D:
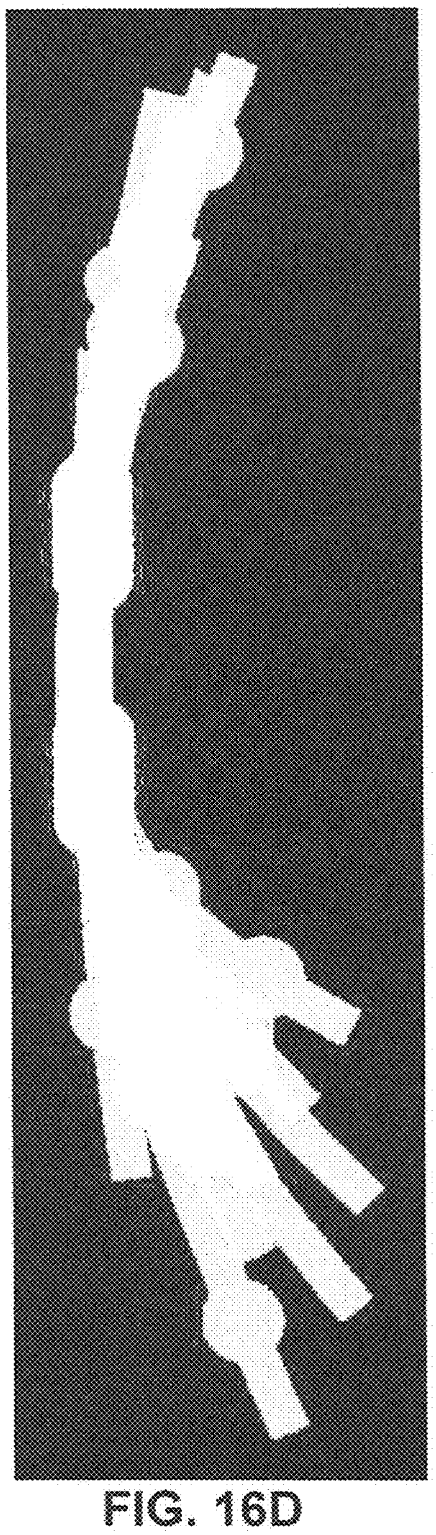
FIG. 16D shows an overlay of 38 patents' rod shapes for fusing from L4 to L5.

The code of the software has been written in-house, and the large data for training is also owned in-house. During training of the layers of the convolutional neural network, various layers and designs were tested to achieve best outcomes. Rod shapes from three different data sources were superimposed using machine learning/Artificial intelligence and overlapping rods with tulips positions were generated under six different rod shapes based on patient specific morphology. FIG. 16A shows an overlay of 7 patients' rod shapes for fusing from S1 to L3 (at least 4 vertebrae fused). FIG. 16B shows an overlay of 4 patients' rod shapes for fusing from L5 to L2. FIG. 16C shows an overlay of 6 patients' rod shapes for fusing from L4 to L2. FIG. 16D shows an overlay of 38 patents' rod shapes for fusing from L4 to L5. The training intervals were repeated, then test data was input to determine if the output would match (known) optimum configurations.

Experimentation with various parameters has been done. FIG. 17A shows three parameters that can be used to identify the intersection point of the tulip head of the pedicle screw and the rod, namely: angulation superior endplate versus screw (positive: screw aiming down; negative: screw aiming up); posterior offset between postero-superior corner and screw head (parallel to superior endplate) in mm; and distal offset between postero-superior corner and screw head (perpendicular to superior endplate) in mm. FIG. 17B shows an illustration used in some embodiments to define sacral slope (SS), pelvic tilt (PT), and pelvic incidence, along with relations among these (e.g., PI=SS+PT).

An example of the machine learning training is shown in FIG. 3I. Into the machine learning algorithm, we input historical patient database (from ideal surgical outcomes and non-ideal) for algorithm training (i.e., large datasets) at 805. For validation or test data we input one patient's data for spinal landmarks, e.g., vertebrae positions, pelvic incidence, and any additional landmarks at 810. The software (see screenshots) outputs planned rod shapes, sizes, tulip head positions, and cage shapes at 815. We (the surgeon) checks output and, if needed, provides adjustments to shapes/positions (human guided training) at 820. After this inspection at 825, the data can proceed to patient implementation at 830 or go back to retrain the AI algorithm at 826. At 830, we utilize planned shapes/positions in actual surgery and add to large dataset (after one to five years post-operative assessment).

Statistical analysis is included in the software, for example, in version 26 of the software, statistical analyses and graphical representation data are presented as means±standard deviation (SD) or standard error of the mean (SEM). The relations between groups are compared using two-tailed, paired Student's T tests or one-way ANOVA tests. Survival is analyzed with the Kaplan-Meier method and was compared with the log-rank test. For multiple testing, Tukey's or Benjamini-Hochberg's methods are employed. Statistical significance is reported as follows: $p \leq 0.05$: *, $p \leq 0.01$: , and $p \leq 0.001$: *.

Example 4. Integration of Manufacturing Methods for the Designs

The proprietary software discussed in Example 2 and Example 3 was interfaced with computer-aided design (CAD) compatible coordinates so that the output designs of the software can be easily manufactured by 3D-printing, milling (e.g., jet), forging, or any other technique known in the art.

Figure 13:
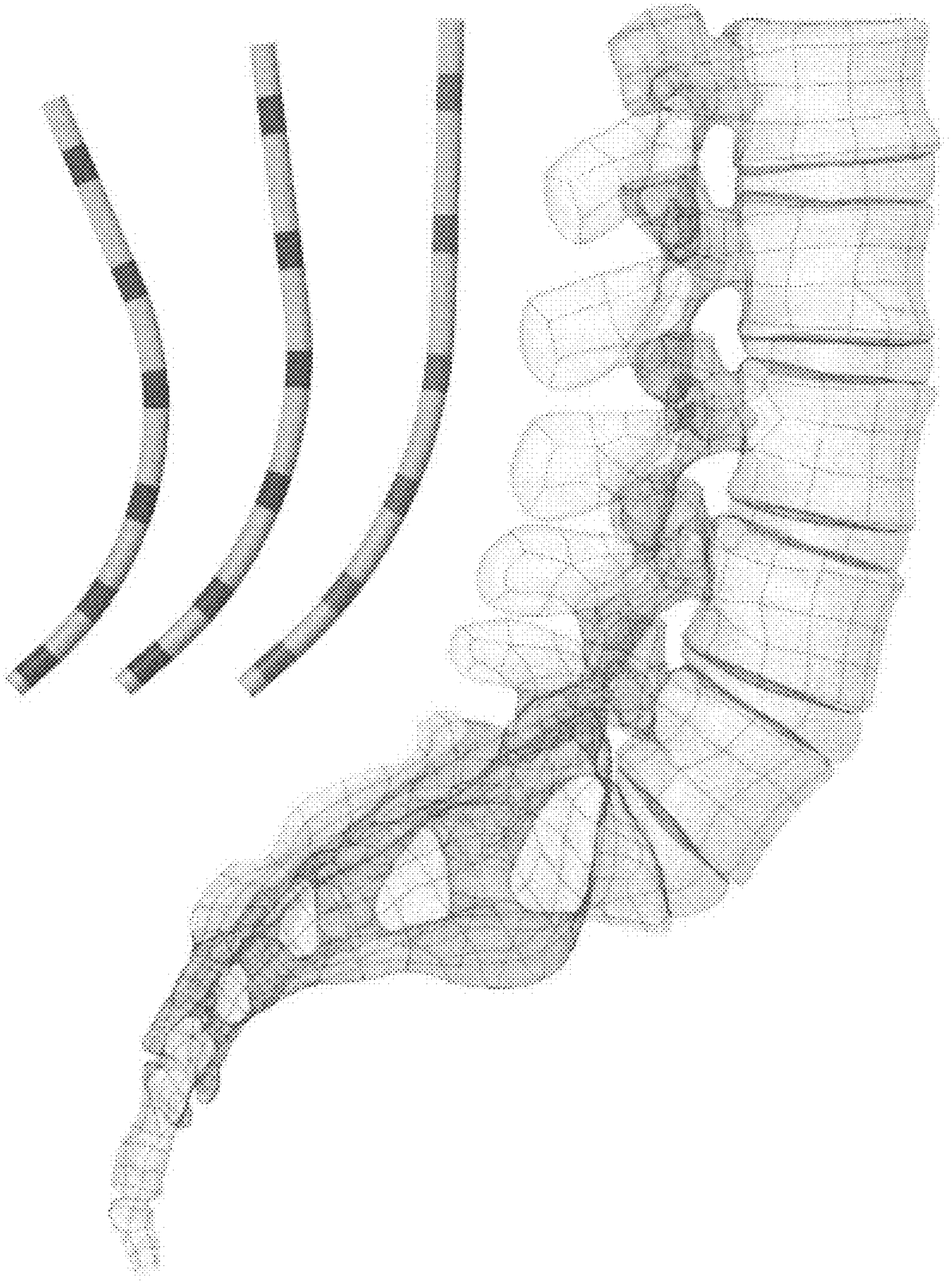
FIG. 13 shows examples of embodiments (at left) wherein demarcations, markings, or bands having a darker color (e.g., blue, black, or purple) are formed on the rod in certain spaced locations along the length of the rod.
Figure 14A:
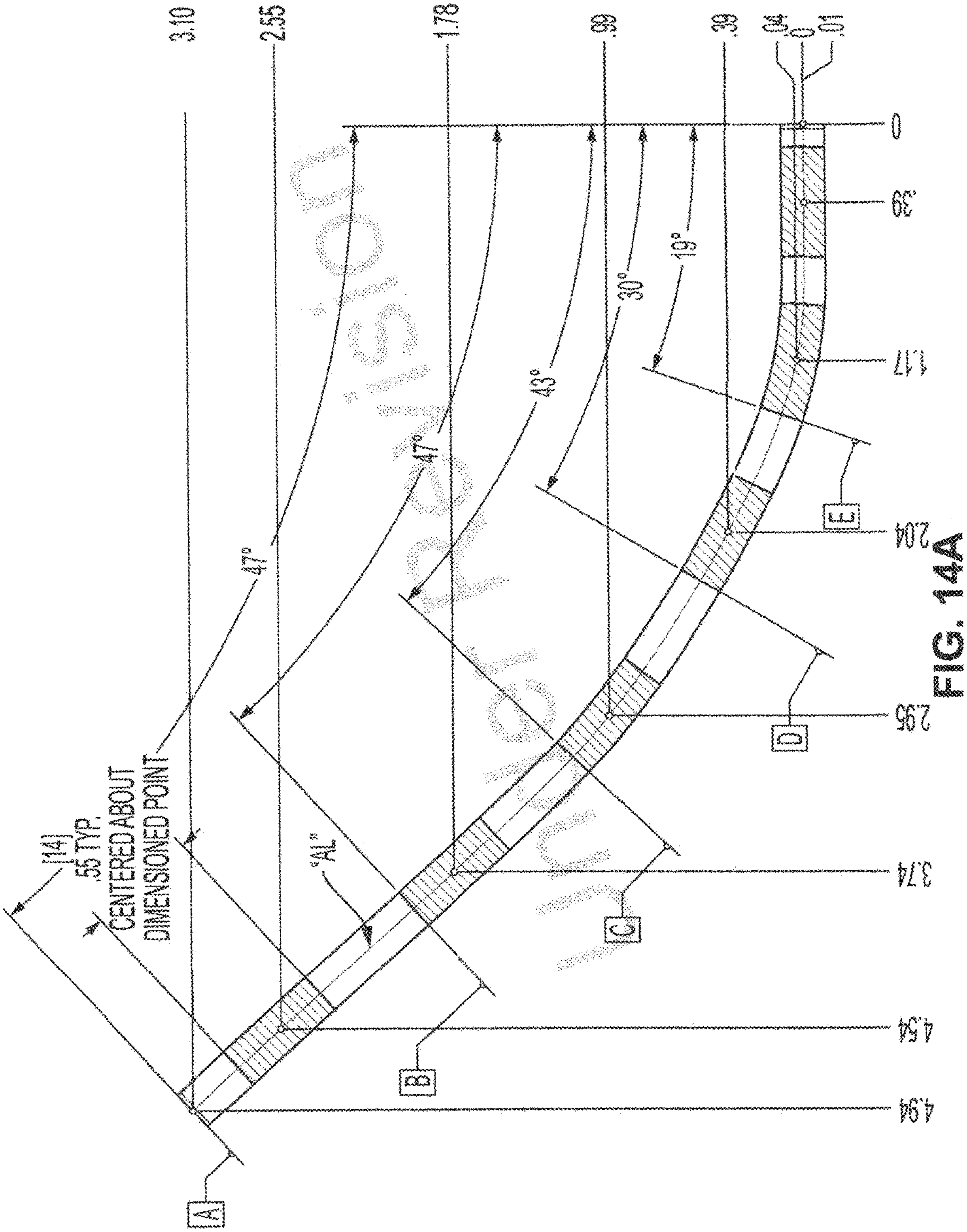
FIG. 14A shows additional examples of embodiments of intelligently placed markings on a rod that enable the surgeon to properly line the rod up to where the rod meets a pedicle screw (as dictated by the patient's anatomy) during surgery and then connect the rod to the tulip head of the pedicle screw in a very precise manner. The markings in FIG. 13 or in FIG. 14A can optionally be utilized as markings indicating to a surgeon where to cut a rod.
Figure 14B:
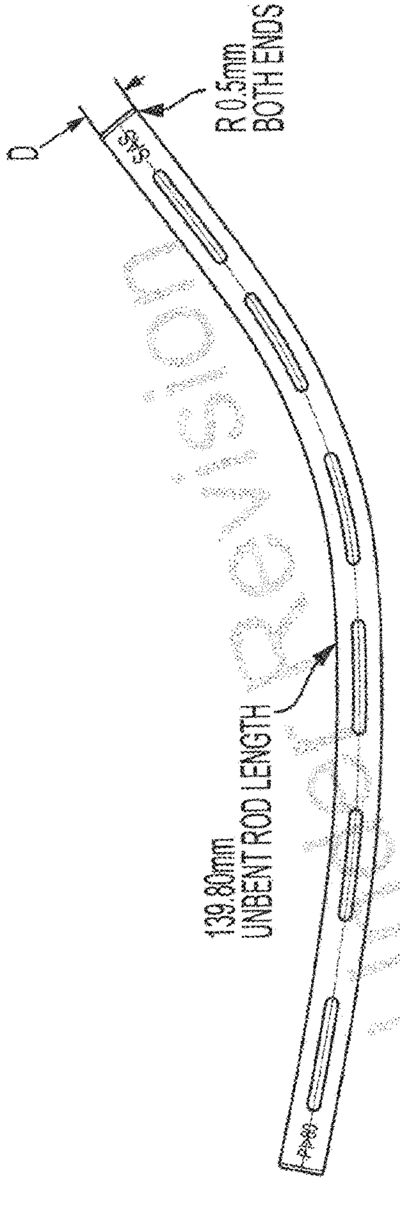
FIG. 14B, FIG. 14C, FIG. 14D, and FIG. 14E show prototypes for various patients illustrating the unique shapes.
Figure 14C:
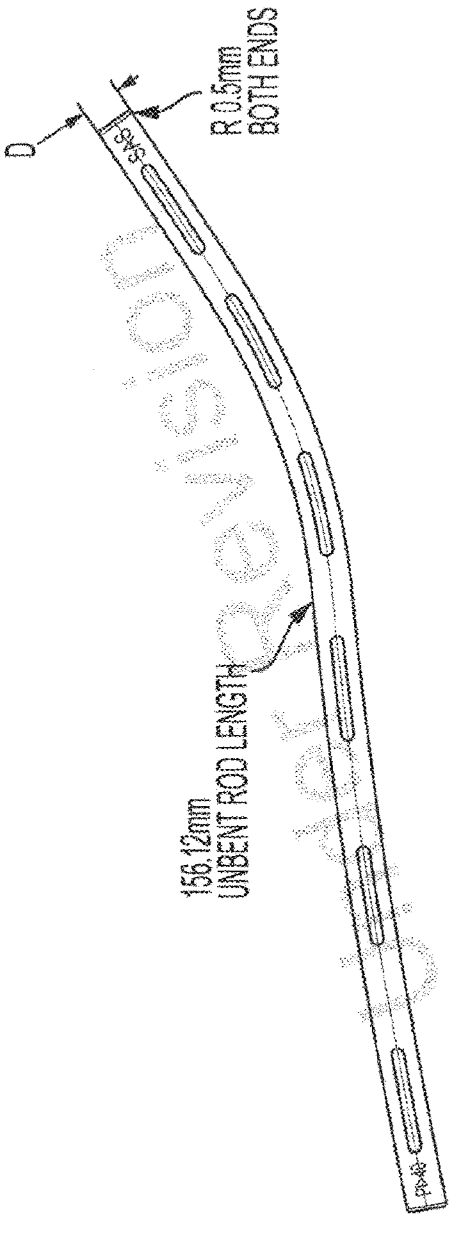
Figure 14D:
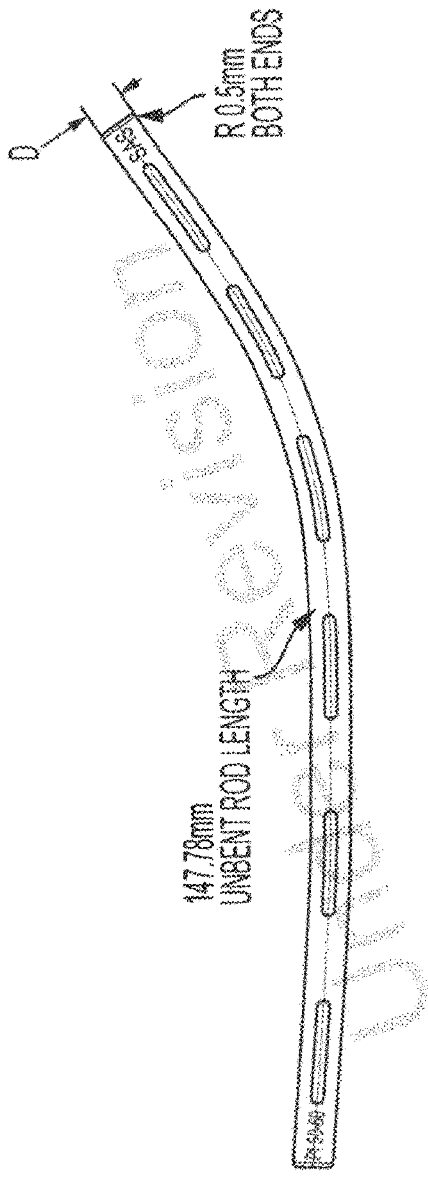
Figure 14E:
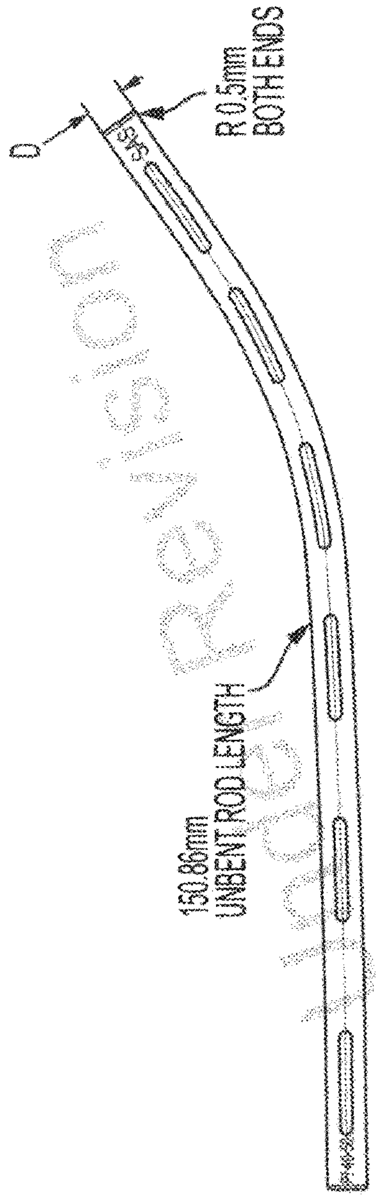
Figure 15A:
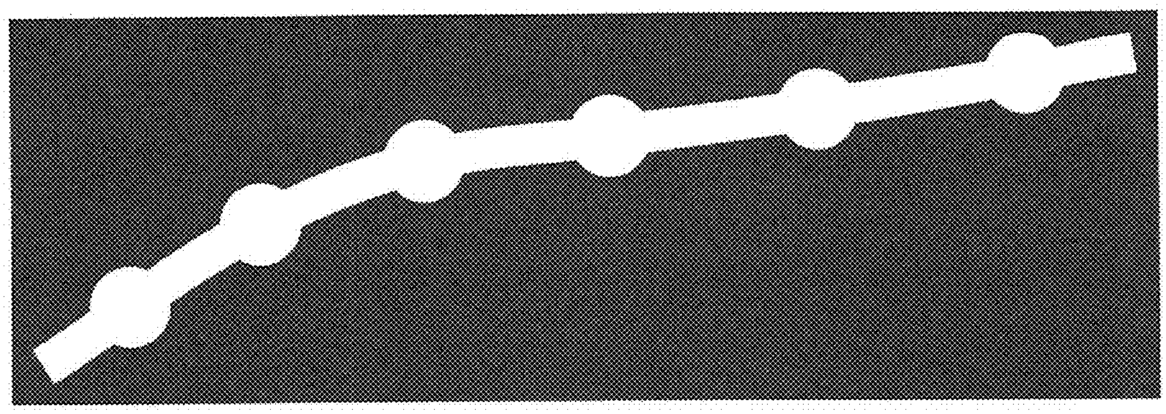
FIG. 15A, FIG. 15B, FIG. 15C, FIG. 15D, FIG. 15E, and FIG. 15F show examples of pelvic incidence rods (PI-Rods) (e.g., rods having PI Categories that cover pelvic incidence angulations of 40, 50, 60, 70, 80 and 90 degrees).
Figure 15B:
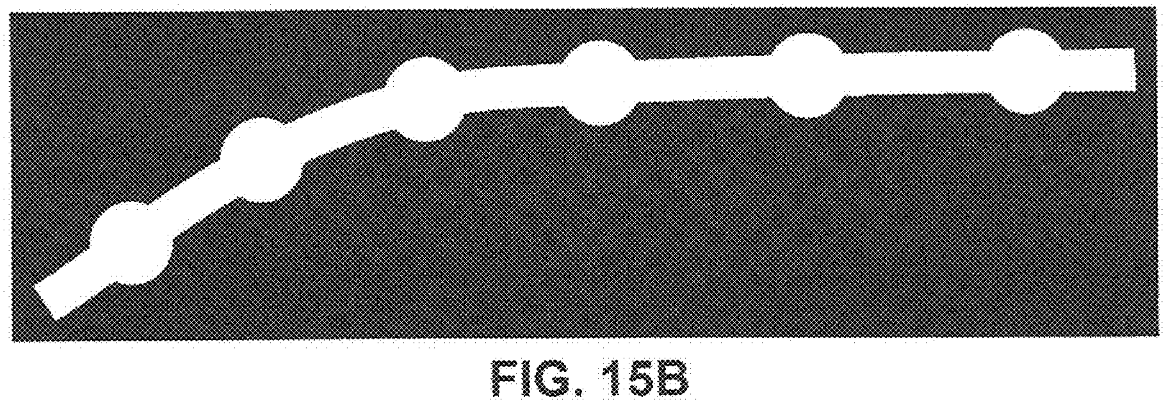
Figure 15C:
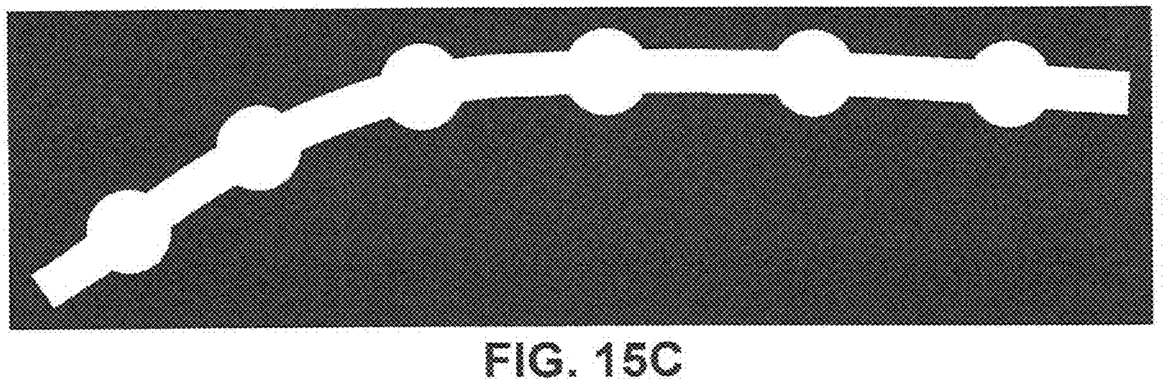
Figure 15D:
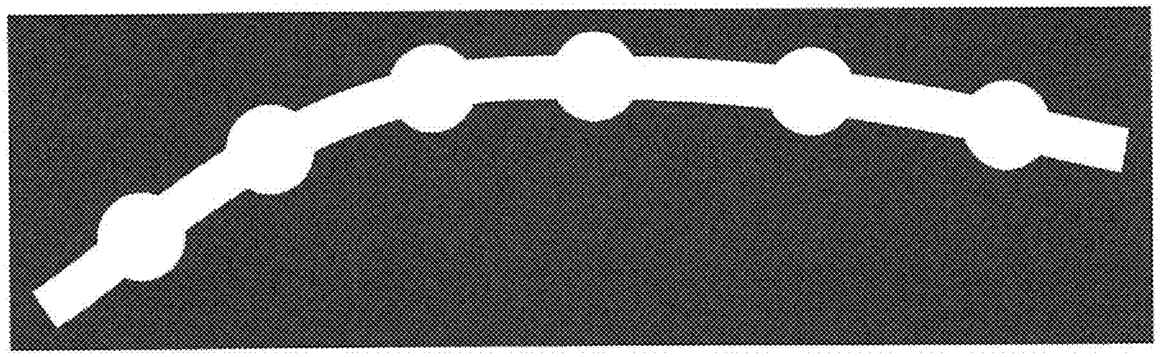
Figure 15E:
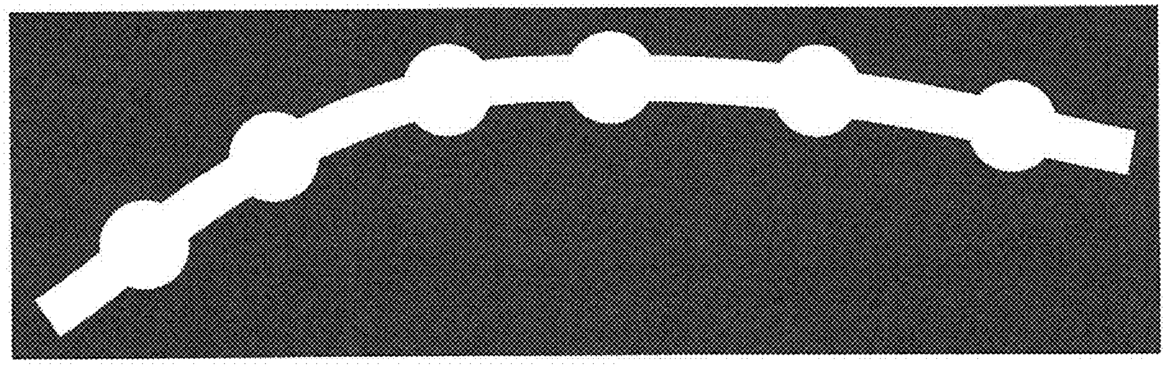
Figure 15F:
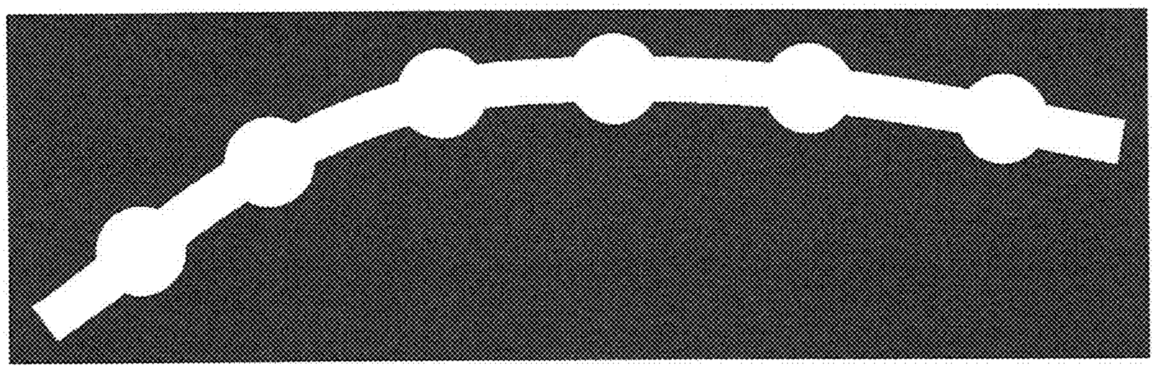

Techniques for placing marks on the rods were compared. FIG. 13 shows examples of embodiments (at left) wherein demarcations, markings, or bands having a darker color (e.g., blue, black, or purple) are formed on the rod in certain spaced locations along the length of the rod. Actual computer-aided design compatible figures are shown in FIG. 14A, which shows additional examples of embodiments of intelligently placed markings on a rod that enable the surgeon to properly line the rod up to where the rod meets a pedicle screw (as dictated by the patient's anatomy) during surgery and then connect the rod to the tulip head of the pedicle screw in a very precise manner. The markings in FIG. 13 or in FIG. 14A can optionally be utilized as markings indicating to a surgeon where to cut a rod. FIG. 14B, FIG. 14C, FIG. 14D, and FIG. 14E show prototypes for various patients illustrating the unique shapes. The markings enable the surgeon to avoid randomly or otherwise imprecisely so-called "eye-balling" or "guesstimating" the placement of the rod relative to the pedicle screw, as practiced with straight and pre-bent rods that are currently available and that have no markings on them.

Example steps leading up to a manufacturing are illustrated in FIG. 3H. At 705, we digitize/scan/denote a plurality of spinal landmarks and/or vertebrae from the spine of a subject in need of surgery (automated, optionally on a computer display). We apply a machine learning algorithm to determine optimum planned positions for the landmarks and/or vertebrae after surgery at 710. The algorithm is utilized to form a shape of a spinal rod to hold the vertebrae in the optimum planned positions after surgery at 715. The AI denotes markers on the rod shape(s) to indicate optimum tulip head positions to align with the optimum positions for the vertebrae after surgery at 720. Utilizing the machine learning algorithm, the system determines optimum shapes/sizes of one or more spinal fusion cages at 725. Exporting of the design specifications for the rods, cages, and markings to a suitable manufacturing process, CAD, or 3D printing is at 730.

Figure 11:
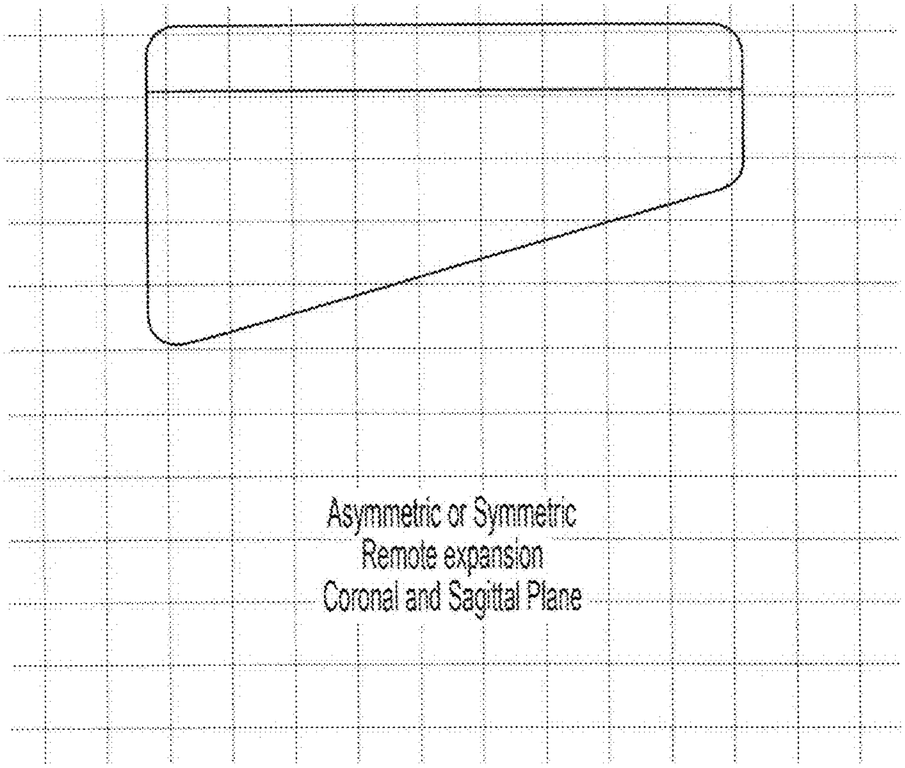
FIG. 11 shows features of a remote expansion capability, which can be implemented in any of the implants or methods disclosed herein.
Figure 12:
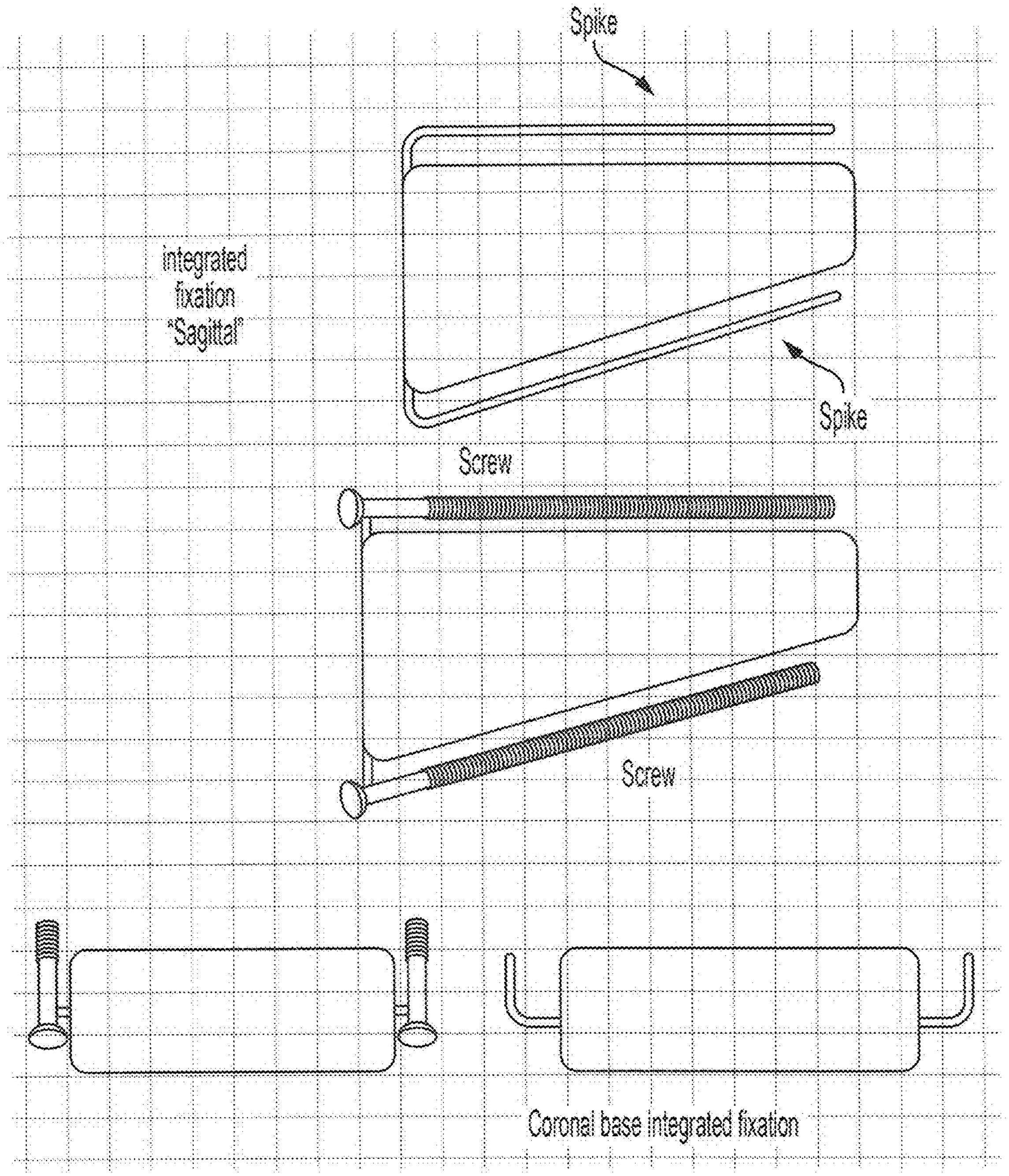
FIG. 12 illustrates spike or screw based integrated fixation of an implant "sagittal" and/or a "coronal" based integrated fixation of an implant.

In a prophetic example, the devices illustrated in FIG. 11 and in FIG. 12 are made and tested along with production of the rods herein. Already, the proprietary software and algorithms in the Examples have enabled intelligent machine learning design of orthopedic implants and methods for using same to replace any "analog" or on the fly design required by a surgeon during such delicate surgeries that have long-term (or lifetime) effects on the patients.

REFERENCES

[1] MedlinePlus. Spinal fusion—series-Pedicle screw. https://medlineplus.gov/ency/presentations/100121_6.htm. Accessed Jan. 30, 2024.

[2]. IUPAC. International Union of Pure and Applied Chemistry GoldBook. https://goldbook.iupac.org/.

[3] Merriam-Webster's Online Dictionary. https://www.merriam-webster.com/.
[4] Porter R. S., & Kaplan, J. L. (Eds.). *The Merck manual of diagnosis and therapy* (19th ed.). Merck Sharp & Dohme Corp. 2011, (978-0-911910-19-3).
[5] Robert S. Porter et al., (eds.). *The Encyclopedia of Molecular Cell Biology and Molecular Medicine*. Blackwell Science Ltd.; 1999-2012, (9783527600908).
[6]. Robert A. Meyers (ed.). *Molecular Biology and Biotechnology: A Comprehensive Desk Reference*. VCH Publishers, Inc.; 1995, (1-56081-569-8).
7. Luttmann Werner. *Immunology*. Elsevier; 2006,
8. Kenneth Murphy Allan Mowat, Casey Weaver (eds.). *Janeway's Immunobiology*. Taylor & Francis Limited; 2014, (9780815345305).
[9]. Krebs Jocelyn E., et al. *Lewin's genes XI*. 11th ed. Burlington, Mass.: Jones & Bartlett Learning; 2014, (1449659055).
[10]. Green Michael R. *Molecular cloning: a laboratory manual/Michael R. Green, Joseph Sambrook*. Cold Spring Harbor, N.Y: Cold Spring Harbor Laboratory Press; 2012, (1936113414).
[11]. Davis et al. *Basic Methods in Molecular Biology*. Elsevier Science Publishing, Inc.; 2012, (044460149X).
[12]. Jon Lorsch (ed.). *Laboratory Methods in Enzymology: DNA*. Elsevier; 2013, (0124199542).
[13]. Frederick M. Ausubel (ed.). *Current Protocols in Molecular Biology* (*CPMB*). John Wiley and Sons 2014, (9780471503385).
[14]. John E. Coligan (ed.). *Current Protocols in Protein Science* (*CPPS*). John Wiley and Sons, Inc.; 2005,
[15]. John E. Coligan ADA M Kruisbeek, David H Margulies, Ethan M Shevach, Warren Strobe, (eds.) *Current Protocols in Immunology* (*CPI*). John Wiley and Sons, Inc.; 2003, (9780471142737).
[16]. Legaye J., et al. Pelvic incidence: a fundamental pelvic parameter for three-dimensional regulation of spinal sagittal curves. *Eur Spine J.* 1998; 7(2):99-103.
[17]. Bach K., et al. Morphometric Analysis of Lumbar Intervertebral Disc Height: An Imaging Study. *World Neurosurg*. 2018.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The foregoing written specification is considered to be sufficient to enable one skilled in the art to practice the present aspects and embodiments. The present aspects and embodiments are not to be limited in scope by examples provided, since the examples are intended as a single illustration of one aspect and other functionally equivalent embodiments are within the scope of the disclosure. Various modifications in addition to those shown and described herein will become apparent to those skilled in the art from the foregoing description and fall within the scope of the appended claims. The advantages and objects described herein are not necessarily encompassed by each embodiment. Those skilled in the art will recognize or be able to ascertain using no more than routine experimentation, many equivalents to the specific embodiments described herein. Such equivalents are intended to be encompassed by the following exemplary claims.

We claim:

1. A pre-contoured spinal fixation rod comprising:

an elongated biocompatible body having a permanent curvature that, when indexed to lumbar spinal levels, provides a distribution of segmental lordosis angles across at least L1-L2, L2-L3, L3-L4, L4-L5, and L5-S1 corresponding to a selected one of six pelvic incidence categories comprising <40°, 40-50°, 50-60°, 60-70°, 70-80°, and >80°; and a plurality of permanent, visually contrasting bands formed at two or more spaced positions along the body that coincide with planned tulip-head seating locations for corresponding vertebral levels, wherein the bands are positioned to align the rod within tulip heads such that, at each corresponding vertebral level, one or more screw angulations relative to a corresponding superior endplate and posterior and distal offsets of the tulip head with respect to a postero-superior corner of the vertebral body are satisfied when the rod is seated in the tulip heads.

2. The spinal fixation rod of claim 1, wherein the rod has a designed stiffness, malleability, and shape, and comprises one or more custom materials selected to achieve the designed stiffness and malleability.

3. The spinal fixation rod of claim 1, wherein the rod comprises a material having a reduced stiffness for use in subjects with weak bone quality to reduce risk of bone damage.

4. The spinal fixation rod of claim 1, wherein the rod comprises one or more of titanium alloys, cobalt-chrome alloys, or another biocompatible material approved by a health authority.

5. The spinal fixation rod of claim 1, wherein the permanent curvature corresponds to a rod shape determined from image-processing software output based on the subject's pelvic morphology and PI (pelvic incidence).

* * * * *